(12) United States Patent
Suresh

(10) Patent No.: US 12,298,193 B2
(45) Date of Patent: May 13, 2025

(54) SPLIT BRIDGE CIRCUIT FORCE SENSOR

(71) Applicant: Intuitive Surgical Operations, Inc., Sunnyvale, CA (US)

(72) Inventor: Ashwinram Suresh, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 18/608,258

(22) Filed: Mar. 18, 2024

(65) Prior Publication Data

US 2024/0302227 A1 Sep. 12, 2024

Related U.S. Application Data

(63) Continuation of application No. 17/885,370, filed on Aug. 10, 2022, now Pat. No. 11,965,789, which is a continuation of application No. 16/763,976, filed as application No. PCT/US2018/061113 on Nov. 14, 2018, now Pat. No. 11,460,360.

(Continued)

(51) Int. Cl.
*G01L 1/22* (2006.01)
*A61B 90/00* (2016.01)
*G01L 5/1627* (2020.01)

(52) U.S. Cl.
CPC ............ *G01L 1/2262* (2013.01); *A61B 90/06* (2016.02); *G01L 1/2281* (2013.01); *G01L 1/2287* (2013.01); *G01L 5/1627* (2020.01); *A61B 2090/064* (2016.02)

(58) Field of Classification Search
CPC ... G01L 1/2262; G01L 1/2281; G01L 1/2287; G01L 5/1627; G01L 19/04; A61B 90/06; A61B 2090/064; A61B 34/30

USPC ........ 73/1.11, 1.15, 763, 765–767, 769, 773, 73/777, 862.473, 862.474,
(Continued)

(56) References Cited

U.S. PATENT DOCUMENTS 2,927,292 A  3/1960  Hunt et al.
3,372,611 A  3/1968  Amanti et al.
(Continued)

FOREIGN PATENT DOCUMENTS

CH  371907 A  9/1963
CN  202158916 U  3/2012
(Continued)

OTHER PUBLICATIONS

Office Action for EP Application No. 18879001.8, mailed Apr. 15, 2024, 5 Pages.
(Continued)

*Primary Examiner* — Robert R Raevis

(57) ABSTRACT

A force sensor comprising a beam having a longitudinal axis and a proximal end portion and a distal end portion; a first Wheatstone bridge disposed on a first face of the beam, including multiple tension gauge resistors and multiple compression gauge resistors; a second Wheatstone bridge disposed on the first face of the beam, including multiple tension gauge resistors and multiple compression gauge resistors; wherein at least one tension gauge resistor and at least one compression gauge resistor from each of the first and second Wheatstone bridges is disposed at a proximal end portion of the beam; wherein at least one tension gauge resistor and at least one compression gauge resistor from each of the first and second Wheatstone bridges is disposed at a distal end portion of the beam.

20 Claims, 13 Drawing Sheets

Related U.S. Application Data

(60) Provisional application No. 62/586,721, filed on Nov. 15, 2017, provisional application No. 62/586,166, filed on Nov. 14, 2017.

(58) Field of Classification Search
USPC ....... 73/862.621–862.623, 862.627–862.634, 73/497, 514.33; 338/7, 8, 36, 46, 47
See application file for complete search history.

(56) References Cited

U.S. PATENT DOCUMENTS

| | | |
|---|---|---|
| 3,878,713 A | 4/1975 | Mole |
| 3,929,009 A | 12/1975 | Lutz et al. |
| 3,985,025 A | 10/1976 | Ormond |
| 3,993,166 A | 11/1976 | Senour |
| 4,034,778 A | 7/1977 | Sage et al. |
| 4,094,192 A | 6/1978 | Watson et al. |
| 4,107,986 A | 8/1978 | Jones |
| 4,223,752 A | 9/1980 | Belcher |
| 4,329,878 A | 5/1982 | Utner et al. |
| 4,331,035 A | 5/1982 | Eisele et al. |
| 4,343,198 A | 8/1982 | Jendrzejczyk |
| 4,369,663 A | 1/1983 | Venturello et al. |
| 4,419,734 A | 12/1983 | Wolfson et al. |
| 4,428,976 A | 1/1984 | Eisele et al. |
| 4,448,083 A | 5/1984 | Hayashi |
| 4,456,293 A | 6/1984 | Panissidi |
| 4,522,072 A | 6/1985 | Sulouff et al. |
| 4,555,955 A | 12/1985 | Morgan et al. |
| 4,640,138 A | 2/1987 | Meyer et al. |
| 4,657,097 A | 4/1987 | Griffen |
| 4,762,006 A | 8/1988 | Asakawa et al. |
| 4,763,531 A | 8/1988 | Dietrich et al. |
| 4,777,826 A | 10/1988 | Rud, Jr. et al. |
| 4,787,256 A | 11/1988 | Cherbuy et al. |
| 4,869,113 A | 9/1989 | Sarrazin |
| 4,906,907 A | 3/1990 | Tsuchihashi et al. |
| 4,932,253 A | 6/1990 | McCoy |
| 5,237,253 A | 8/1993 | Moreau et al. |
| 5,327,791 A | 7/1994 | Walker |
| 5,347,871 A | 9/1994 | D'Andrea et al. |
| 5,513,536 A | 5/1996 | Reger et al. |
| 5,723,826 A | 3/1998 | Kitagawa et al. |
| 5,767,840 A | 6/1998 | Selker |
| 5,784,542 A | 7/1998 | Ohm et al. |
| 5,855,583 A | 1/1999 | Wang et al. |
| 5,889,214 A | 3/1999 | Kang et al. |
| 5,894,094 A | 4/1999 | Kuchler et al. |
| 5,969,268 A | 10/1999 | Sommerfeld et al. |
| 6,038,933 A | 3/2000 | Meyer |
| 6,197,017 B1 | 3/2001 | Brock et al. |
| 6,331,181 B1 | 12/2001 | Tierney et al. |
| 6,394,998 B1 | 5/2002 | Wallace et al. |
| 6,459,926 B1 | 10/2002 | Nowlin et al. |
| 6,494,882 B1 | 12/2002 | Lebouitz et al. |
| 6,532,830 B1 | 3/2003 | Jansen et al. |
| 6,594,552 B1 | 7/2003 | Nowlin et al. |
| 6,675,663 B1 | 1/2004 | Irion et al. |
| 6,763,716 B2 | 7/2004 | Nagahara et al. |
| 6,817,974 B2 | 11/2004 | Cooper et al. |
| 6,835,173 B2 | 12/2004 | Couvillon, Jr. |
| 6,871,552 B2 | 3/2005 | Liu et al. |
| 6,902,560 B1 | 6/2005 | Morley et al. |
| 6,910,392 B2 | 6/2005 | Lockery et al. |
| 6,936,042 B2 | 8/2005 | Wallace et al. |
| 6,979,873 B2 | 12/2005 | Fujii |
| 6,994,708 B2 | 2/2006 | Manzo |
| 7,083,571 B2 | 8/2006 | Wang et al. |
| 7,169,141 B2 | 1/2007 | Brock et al. |
| 7,174,792 B2 | 2/2007 | Ealey |
| 7,302,139 B1 | 11/2007 | Ames |
| 7,437,954 B2 | 10/2008 | Sakano |
| 7,441,470 B2 | 10/2008 | Morimoto |
| 7,500,406 B2 | 3/2009 | Morimoto |
| 7,578,219 B2 | 8/2009 | Wu |
| 7,594,445 B2 | 9/2009 | Hirabayashi et al. |
| 7,603,917 B2 | 10/2009 | Graham et al. |
| 7,665,371 B2 | 2/2010 | Mastinu et al. |
| 7,743,672 B2 | 6/2010 | Kurtz et al. |
| 7,779,705 B2 | 8/2010 | Mastinu et al. |
| 7,935,130 B2 | 5/2011 | Williams |
| 8,281,670 B2 | 10/2012 | Larkin et al. |
| 8,444,631 B2 | 5/2013 | Yeung et al. |
| 8,465,474 B2 | 6/2013 | Blumenkranz |
| 8,479,969 B2 | 7/2013 | Shelton, IV |
| 8,491,574 B2 | 7/2013 | Blumenkranz |
| 8,496,647 B2 | 7/2013 | Blumenkranz et al. |
| 8,506,555 B2 | 8/2013 | Ruiz Morales |
| 8,551,115 B2 | 10/2013 | Steger et al. |
| 8,561,473 B2 | 10/2013 | Blumenkranz |
| 8,602,288 B2 | 12/2013 | Shelton, IV et al. |
| 8,620,473 B2 | 12/2013 | Diolaiti et al. |
| 8,621,939 B2 | 1/2014 | Blumenkranz et al. |
| 8,628,518 B2 | 1/2014 | Blumenkranz et al. |
| 8,771,270 B2 | 7/2014 | Burbank |
| 8,800,838 B2 | 8/2014 | Shelton, IV |
| 8,881,597 B2 | 11/2014 | Jost et al. |
| 8,945,095 B2 | 2/2015 | Blumenkranz et al. |
| 9,028,494 B2 | 5/2015 | Shelton, IV et al. |
| 9,101,734 B2 | 8/2015 | Selkee |
| 9,192,448 B2 | 11/2015 | Blumenkranz |
| 9,204,923 B2 | 12/2015 | Manzo et al. |
| 9,232,979 B2 | 1/2016 | Parihar et al. |
| 9,707,684 B2 | 7/2017 | Ruiz et al. |
| 9,782,214 B2 | 10/2017 | Houser et al. |
| 9,855,102 B2 | 1/2018 | Blumenkranz |
| 9,952,107 B2 | 4/2018 | Blumenkranz et al. |
| 10,085,809 B2 | 10/2018 | Blumenkranz et al. |
| 10,390,896 B2 | 8/2019 | Blumenkranz |
| 10,620,066 B2 | 4/2020 | Blumenkranz et al. |
| 10,967,934 B2 | 4/2021 | Ferguson |
| 11,460,360 B2 | 10/2022 | Suresh |
| 2003/0140713 A1 | 7/2003 | Ohsato et al. |
| 2003/0150276 A1 | 8/2003 | Christensen et al. |
| 2005/0050960 A1 | 3/2005 | Haines |
| 2005/0103123 A1 | 5/2005 | Newman |
| 2006/0070464 A1 | 4/2006 | Walker |
| 2007/0096666 A1 | 5/2007 | Ippisch |
| 2007/0151391 A1 | 7/2007 | Larkin et al. |
| 2008/0047366 A1 | 2/2008 | Kuriyama et al. |
| 2008/0065111 A1 | 3/2008 | Blumenkranz et al. |
| 2008/0295610 A1 | 12/2008 | Inamori |
| 2009/0248038 A1 | 10/2009 | Blumenkranz et al. |
| 2009/0320610 A1 | 12/2009 | Ohsato et al. |
| 2009/0324161 A1 | 12/2009 | Prisco |
| 2010/0024574 A1 | 2/2010 | Werthschutzky et al. |
| 2010/0219388 A1 | 9/2010 | Schena |
| 2010/0324453 A1 | 12/2010 | Lal et al. |
| 2011/0071543 A1 | 3/2011 | Prisco et al. |
| 2011/0282356 A1 | 11/2011 | Solomon et al. |
| 2013/0282024 A1 | 10/2013 | Blumenkranz |
| 2014/0257333 A1 | 9/2014 | Blumenkranz |
| 2015/0021105 A1 | 1/2015 | Head et al. |
| 2015/0075250 A1 | 3/2015 | Kosa et al. |
| 2015/0135832 A1 | 5/2015 | Blumenkranz et al. |
| 2015/0330856 A1 | 11/2015 | Chiou et al. |
| 2015/0374447 A1 | 12/2015 | Blumenkranz et al. |
| 2015/0374449 A1 | 12/2015 | Chowaniec et al. |
| 2016/0146685 A1 | 5/2016 | Chiou et al. |
| 2017/0261306 A1 | 9/2017 | Ausserlechner et al. |
| 2017/0307457 A1 | 10/2017 | Zwijze et al. |
| 2018/0067003 A1 | 3/2018 | Michiwaki |
| 2019/0069966 A1 | 3/2019 | Petersen et al. |
| 2019/0336229 A1 | 11/2019 | Blumenkranz |
| 2020/0129261 A1 | 4/2020 | Eschbach |
| 2022/0390300 A1 | 12/2022 | Suresh |

FOREIGN PATENT DOCUMENTS

| | | |
|---|---|---|
| CN | 107532961 A | 1/2018 |
| CN | 108603799 A | 9/2018 |
| CN | 110160681 A | 8/2019 |
| DE | 2802176 A1 | 7/1979 |

(56) References Cited

FOREIGN PATENT DOCUMENTS

| | | |
|---|---|---|
| DE | 3405168 A1 | 8/1985 |
| DE | 19523523 A1 | 1/1996 |
| DE | 10013059 A1 | 9/2001 |
| DE | 202007010974 U1 | 10/2007 |
| EP | 0244324 B1 | 7/1989 |
| EP | 1965717 B1 | 5/2012 |
| EP | 2289455 B1 | 11/2019 |
| ES | 2000423 A4 | 3/1988 |
| FR | 2598226 B1 | 4/1989 |
| FR | 2693397 A1 | 1/1994 |
| GB | 2293453 B | 10/1996 |
| GB | 2475081 A | 5/2011 |
| JP | S51127776 A | 11/1976 |
| JP | S5612526 A | 2/1981 |
| JP | H02223836 A | 9/1990 |
| JP | H0514871 U | 2/1993 |
| JP | H05172661 A | 7/1993 |
| JP | H06174565 A | 6/1994 |
| JP | H07190865 A | 7/1995 |
| JP | H0875572 A | 3/1996 |
| JP | H08201202 A | 8/1996 |
| JP | H09257601 A | 10/1997 |
| JP | H09269258 A | 10/1997 |
| JP | 2001153735 A | 6/2001 |
| JP | 2005103056 A | 4/2005 |
| JP | 2005274395 A | 10/2005 |
| JP | 2009541752 A | 11/2009 |
| JP | 5612526 B2 | 10/2014 |
| JP | 5853121 B1 | 2/2016 |
| JP | 2017194467 A | 10/2017 |
| KR | 970004983 A | 1/1997 |
| KR | 100703861 B1 | 4/2007 |
| KR | 20080089582 A | 10/2008 |
| WO | WO-2006006677 A1 | 1/2006 |
| WO | WO-2007111737 A2 | 10/2007 |
| WO | WO-2007120329 A2 | 10/2007 |
| WO | WO-2015120108 A1 | 8/2015 |
| WO | WO-2016159245 A1 | 10/2016 |
| WO | WO-2017023825 A1 | 2/2017 |
| WO | WO-2017136332 A1 | 8/2017 |
| WO | WO-2019099562 A1 | 5/2019 |

OTHER PUBLICATIONS

Chinese Office Action dated Mar. 15, 2022, in Application No. CN201880081139 with English Translation, 33 pages.
Extended European Search Report for Application No. EP18879001.8 mailed on Jul. 6, 2021, 8 pages.
International Search Report and Written Opinion for Application No. PCT/US2018/061113, mailed on Feb. 22, 2019, 22 pages (ISRG11660/PCT).
Mayer H., et al., "Upgrading Instruments for Robotic Surgery," Proceedings of Australasian Conference on Robotics and Automation, 2004, Canberra, Australia, 07 pages.
Notice of Allowance for KR Application No. 10-2020-7013635, mailed Mar. 30, 2022, 4 pages.
Office Action for JP Application No. 2020-526396, mailed Jan. 18, 2022, 12 pages.
Office Action for JP Application No. 2022119361, mailed Dec. 5, 2023, 06 pages.
Office Action for JP Application No. 2022-119361, mailed Jun. 20, 2023, 12 pages.
Office Action for U.S. Appl. No. 17/885,370, mailed Jul. 7, 2023, 05 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.
Extended European Search Report for Application No. EP24210961.9, mailed on Feb. 3, 2025. 11 pages.
Vyroubal D., "A Circuit for Lead Resistance Compensation and Complex Balancing of the Strain-gauge Bridge," IEEE Transactions on Instrumentation and Measurement, Feb. 1993, vol. 42(1), pp. 44-48.

Interleaved Design

SPLIT BRIDGE CIRCUIT FORCE SENSOR

CLAIM OF PRIORITY

This application is a continuation of U.S. application Ser. No. 17/885,370, filed on Aug. 10, 2022, and published as US 2022/0390300 A1 on Dec. 8, 2022, which is a continuation of U.S. application Ser. No. 16/763,976, filed on May 13, 2020, and published as US 2020/0278265 A1 on Sep. 3, 2020 (now U.S. Pat. No. 11,460,360), which is a U.S. National Stage Filing under 35 U.S.C. 371 from International Application No. PCT/US2018/061113, filed on Nov. 14, 2018, and published as WO 2019/099562 A1 on May 23, 2019, which claims the benefit of priority to U.S. Provisional Patent Application Ser. No. 62/586,721, filed on Nov. 15, 2017, and to U.S. Provisional Patent Application Ser. No. 62/586,166, filed on Nov. 14, 2017, each of which is incorporated by reference herein in its entirety.

BACKGROUND

Force sensing and feedback during a minimally invasive surgical procedure may bring better immersion, realism and intuitiveness to a surgeon performing the procedure. For the best performance of haptics rendering and accuracy, force sensors may be placed on a surgical instrument and as close to the anatomical tissue interaction as possible. One approach is to embed a force sensor at a distal end of a surgical instrument shaft with electrical strain gauges formed on the force transducer, through printing or additive deposition processes, to measure strain imparted to the surgical instrument.

FIG. 1 is an illustrative drawing representing a force sensor that includes a rectangular beam with four full-Wheatstone bridges (full-bridges). A bridge circuit is a circuit topology of electrical circuit in which two circuit branches (usually in parallel with each other) are bridged by a third branch connected between the first two branches at some intermediate point along them. Two full-bridges are formed on each of two adjacent orthogonal side faces of the beam to measure forces orthogonal to a longitudinal axis of the beam. The beam may be secured to a distal portion of a surgical instrument shaft to sense forces orthogonal to a longitudinal axis of the shaft. A forces applied orthogonal to a side face of the beam (i.e. an X or Y force) is determined by subtracting force measurements determined by the full-bridges at proximal and distal end portions of that side face of the beam.

A force sensor may experience a variety of different strain sources including: the orthogonal force of interest to be measured, moment, off axis force, off axis moment, compression/tension, torsion, ambient temperature and gradient temperature. Each of the full-bridges cancels the following stress: temperature, torsion, off axis force, and off axis moment. Each individual full-bridge output indicates stress due to force, moment, and compression/tension. The subtraction of an output value produced by a proximal full-bridge formed on a side face from an output value produced by a distal full-bridge on the same side face, cancels the moment and compression/tension, resulting in an output value that represents the orthogonal force of interest to be measured.

A surgical instrument force sensor may be critical to ensuring patient safety. Accordingly, force sensor error detection may be required to protect against harm by detecting force sensor failures. One approach to error detection may be to provide additional full-bridges to produce redundant force measurements that can be compared to detect errors. However, limited space on beam side faces makes formation of additional full-bridges on a side face impractical. Moreover, a manufacturing process typically is limited to formation of bridges at most on two side faces. Formation of bridges on four side faces would increase manufacturing cost significantly.

SUMMARY

In one aspect, a force sensor includes a beam having a longitudinal axis and a proximal end portion and a distal end portion. A first Wheatstone bridge is disposed on a first face of the beam and includes first and second tension gauge resistors and first and second compression gauge resistors. A second Wheatstone bridge is disposed on the first face of the beam and includes third and fourth tension gauge resistors and third and fourth compression gauge resistors. The first and third tension gauge resistors and the first and third compression gauge resistors are disposed at a proximal end portion of the beam. The second and fourth tension gauge resistors and the second and fourth compression gauge resistors are disposed at a distal end portion of the beam.

In another aspect, a force sensor includes a beam having a longitudinal axis and a proximal end portion and a distal end portion. A first tension gauge half-bridge is disposed on a first face of the beam and includes first and second tension gauge resistors. A second tension gauge half-bridge is disposed on the first face of the beam and includes third and fourth tension gauge resistors. A compression gauge half-bridge is disposed on the first face of the beam and includes first and second compression gauge resistors. The first and third tension gauge resistors and the first compression gauge resistor are disposed at a proximal end portion of the beam. The second and fourth tension gauge resistors and the second compression gauge resistor are disposed at a distal end portion of the beam.

In yet another aspect, a force sensor includes a beam having a longitudinal axis and a proximal end portion and a distal end portion. A first bridge circuit is disposed on a first face of the beam and includes multiple tension gauge resistors and at least one compression gauge resistor. A second bridge circuit is disposed on the first face of the beam and includes multiple tension gauge resistors and at least one compression gauge resistor. The at least one tension resistor from each of the first and second bridge circuits and at least one compression gauge resistor from one of the first and second bridges are disposed at a proximal end portion of the beam. The at least one tension resistor from each of the first and second bridge circuits and at least one compression gauge resistor from one of the other of the first and second bridges are disposed at a distal end portion of the beam.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 2:
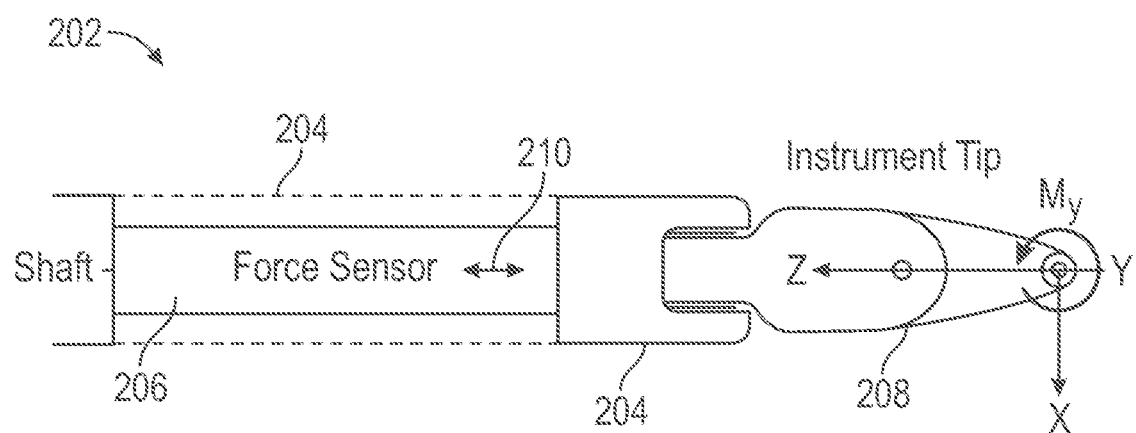
FIG. 2 is an illustrative side elevation view of a distal portion of a surgical instrument with an elongated shaft having a force sensor beam mounted thereon, in accordance with some examples.

FIG. 2 is an illustrative side elevation view of a distal portion of a surgical instrument 202 with an elongated shaft 204, shown in partially cut-way, having a force sensor beam 206 mounted thereon, in accordance with some examples. The surgical instrument 202 includes an end effector 208, which may include articulatable jaws, for example. During a surgical procedure, the end effector 208 contacts anatomical tissue, which may result in X, Y, or Z direction forces and that may result in moment forces such as a moment My about a y-direction axis. The force sensor beam 206, which includes a longitudinal axis 210, may be used to measure X and Y forces perpendicular to the longitudinal axis 210.

Figure 3:
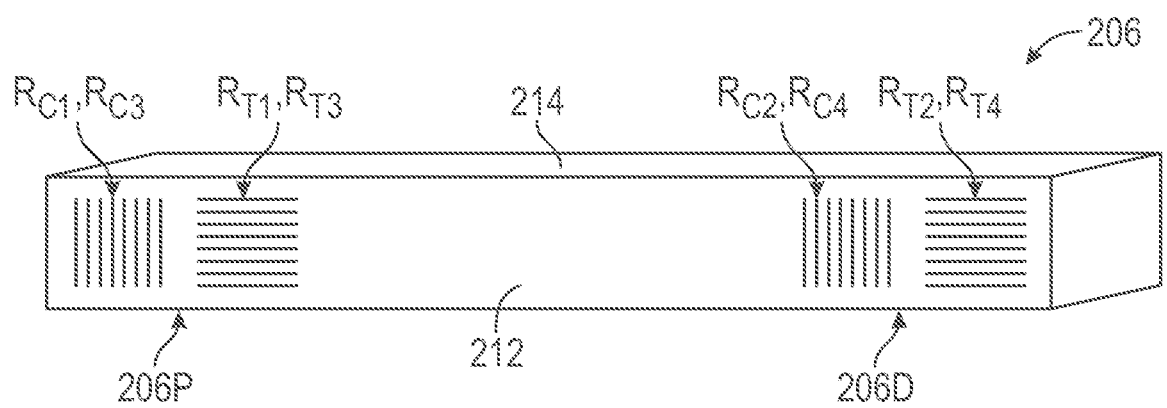
FIG. 3 is an illustrative perspective view of a force sensor beam having a beam side face with a pair of split bridge circuits formed thereon.
Figure 4A:
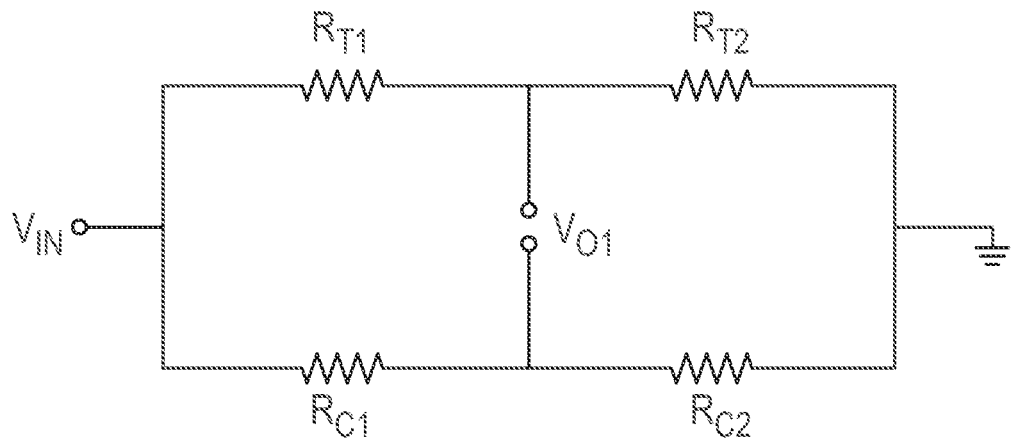
FIG. 4A is an illustrative schematic diagram representative of a first full-bridge bridge circuit.
Figure 4B:
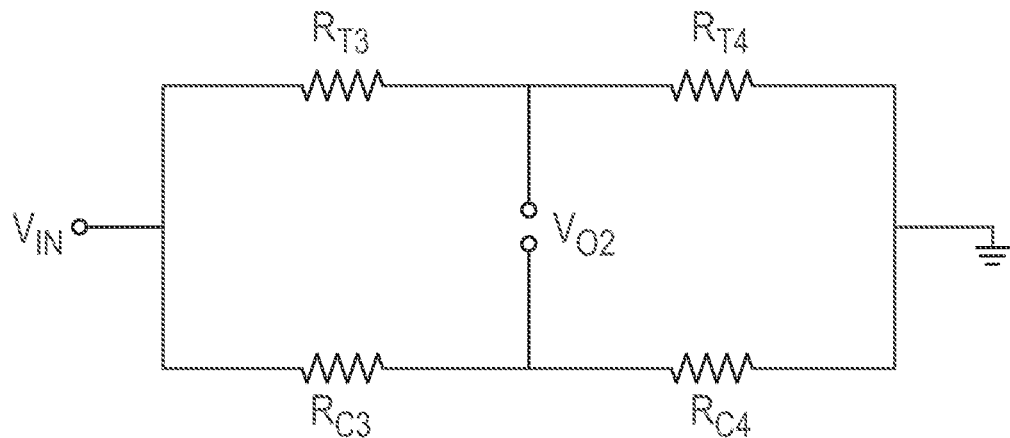
FIG. 4B is an illustrative schematic diagram representative of a second full-bridge circuit.

FIG. 3 is an illustrative perspective view of a force sensor beam 206 having a beam side face 212 with a pair of split bridge circuits formed thereon. The bridge circuits are split in that a portion of each bridge circuit is disposed at a proximal end portion of the beam and a portion of the bridge circuit is disposed at a distal end portion of the beam. More particularly, in the example of FIG. 3, the bridge circuits are configured as interleaved split full-Wheatstone bridges (full-bridges) formed thereon, having strain gauge resistors $R_{C1}$, $R_{C3}$, $R_{T1}$, $R_{T3}$ aligned along a neutral axis (equidistant from the sides of the beam) at a proximal beam end portion 206P and having strain gauge resistors $R_{C2}$, $R_{C4}$, $R_{T2}$, $R_{T4}$ aligned along a neutral axis at a distal beam end portion 206D, in accordance with some examples. An identical pair of interleaved split full-bridges (not shown) is formed on an adjacent orthogonal beam side face 214. The pair of interleaved split full-bridges formed on adjacent orthogonal side faces are configured to measure forces perpendicular to a longitudinal axis 210 of the beam 206, which may impart tensile strain to the beam. It will be appreciated that alignment of the gauge resistors along the neutral axis reduces the effect of off axis load since the neutral axis is insensitive to off axis force and moments FIG. 4A is an illustrative schematic diagram representative of a first split full-bridge bridge of the pair, which includes a tension-gauge half-bridge comprising tension strain gauge resistors $R_{T1}$ and $R_{T2}$ and includes a compression-gauge half-bridge comprising compression strain gauge resistors $R_{C1}$ and $R_{C2}$, coupled as shown to receive an input voltage Vin and to produce a first output voltage $V_{O1}$. FIG. 4B is an illustrative schematic diagram representative of a second split full-bridge of the pair, which includes a tension-gauge half-bridge tension strain gauge resistors $R_{T3}$ and $R_{T4}$ and includes a compression-gauge half-bridge comprising compression strain gauge resistors $R_{C3}$ and $R_{C4}$, coupled as shown to receive the input voltage Vin and to produce a second output voltage $V_{O2}$.

As explained more fully below, each tension strain gauge resistor $R_{T1}$-$R_{T4}$ and each compression strain gauge resistor $R_{C1}$-$R_{C4}$ includes a plurality of elongated resistor portions aligned in parallel and coupled end-to-end to form a serpentine or snake-like configuration. The elongated portions of the compression strain gauge resistors $R_{C1}$-$R_{C4}$ may be aligned perpendicular to the longitudinal axis 210 of the beam to sense compression strain upon the beam 206. The elongated portions of the tension strain gauge resistors $R_{T1}$-$R_{T4}$ may be aligned parallel to the longitudinal axis of the beam to sense tension strain upon the beam.

Referring again to FIG. 3, each interleaved split full-bridge has a tension gauge sensor resistor and a compression gauge sensor resistor disposed at the proximal end portion 206P of the beam 206. Each interleaved split full-bridge also has a tension gauge sensor and a compression gauge sensor disposed at the distal end portion 206D of the beam 206. Specifically, strain gauge resistors, $R_{T1}$, $R_{T3}$ $R_{C1}$ and $R_{C3}$ are disposed at the proximal end portion 206P of the beam 206, and strain gauge resistors $R_{T2}$, $R_{T4}$, $R_{C2}$ and $R_{C4}$ are disposed at the distal end portion 206D of the beam 206. Moreover, elongated portions of strain gauge resistor $R_{T1}$ are interleaved with elongated portions of strain gauge resistor $R_{T3}$ so as to be co-located and occupy same longitudinal region of the beam. Elongated portions of strain gauge resistor $R_{C1}$ are interleaved with elongated portions of strain gauge resistor $R_{C3}$ so as to be co-located and occupy same longitudinal region of the beam. The interleaved compression gauge resistors $R_{C1}$, Res are disposed closer to the proximal end of the beam than the interleaved tension resistors $R_{T1}$, $R_{T3}$. Elongated portions of strain gauge resistor $R_{T2}$ are interleaved with elongated portions of strain gauge resistor $R_{T4}$ so as to be co-located and occupy same longitudinal region of the beam. Elongated portions of strain gauge resistor Rea are interleaved with elongated portions of strain gauge resistor $R_{C4}$ so as to be co-located and occupy same longitudinal region of the beam. The interleaved compression gauge resistors $R_{C2}$, $R_{C4}$ are disposed farther from the distal end of the beam than the interleaved tension resistors $R_{T2}$, $R_{T4}$. The interleaving of strain gauge resistors of the example of FIG. 3 will be better understood from the description with reference to the interleaved half-bridge example represented in the illustrative drawings of FIG. 8.

Figure 5:
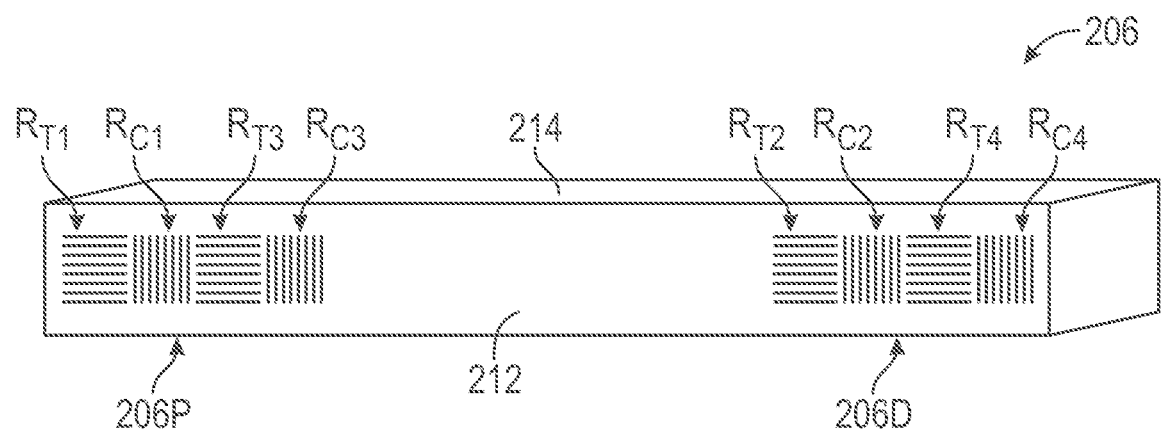
FIG. 5 is an illustrative perspective view of a force sensor beam having a beam side face with a pair of staggered split bridge circuits formed thereon.

FIG. 5 is an illustrative perspective view of a force sensor beam 206 having a beam side face 212 with staggered split full-bridges formed thereon, each having strain gauge resistors $R_{C1}$, $R_{C3}$, $R_{T1}$, $R_{T3}$ aligned along a neutral axis at a proximal beam end portion 206P and each having strain gauge resistors $R_{C2}$, $R_{C4}$, $R_{T2}$, $R_{T4}$ aligned along a neutral axis at a distal beam end portion 206D, in accordance with some examples. The beam has four elongated rectangular side faces and rectangular end faces. An identical pair of staggered split full-bridges (not shown) is formed on an adjacent orthogonal beam side face 214. The pair of staggered split full-bridges formed on adjacent orthogonal side faces are configured to measure forces perpendicular to the longitudinal axis of the beam, which may impart tensile strain to the beam.

The illustrative schematic diagrams of FIGS. 4A-4B, described above, are representative of first and second full-bridges of the staggered split full-bridges of FIG. 5. Each staggered split full-bridge has a tension gauge sensor resistor and a compression gauge sensor resistor disposed at the proximal end portion 206P of the beam 206. Each full-bridge also has a tension gauge sensor and a compression gauge sensor disposed at the distal end portion 206D of the beam 206. Specifically, strain gauge resistors, $R_{T1}$, $R_{T3}$ $R_{C1}$ and $R_{C3}$ are disposed at the proximal end portion 206P of the beam 206, and strain gauge resistors $R_{T2}$, $R_{T4}$, $R_{C2}$ and $R_{C4}$ are disposed at the distal end portion 206D of the beam 206. However, unlike the pair of the interleaved split full-bridges of FIG. 3, the split staggered split bridges of FIG. 5 are disposed in a "staggered" arrangement in which pairs of strain gauges of each full-bridge are disposed adjacent to each other at opposite end portions of the beam. Strain gauge resistors $R_{T1}$ and $R_{C1}$ of the first staggered split full-bridge are disposed adjacent to each other at the proximal end portion 206P of the beam 206. Strain gauge resistors $R_{T3}$ and $R_{C3}$ of the second staggered split full-bridge are disposed adjacent to each other at the proximal end portion 206P of the beam 206, offset farther from the proximal end portion 206B than are the strain gauge resistors $R_{T1}$ and $R_{C1}$. Similarly, strain gauge resistors $R_{T2}$ and $R_{C2}$ of the first staggered split full-bridge are disposed adjacent to each other at the distal end portion 206D of the beam 206. Strain gauge resistors $R_{T4}$ and $R_{C4}$ of the second staggered split full-bridge are disposed adjacent to each other at the distal end portion 206D, offset closer to the distal end portion 206D than are the strain gauge resistors $R_{T2}$ and $R_{C2}$.

Both the interleaved split full-bridge and the staggered split full-bridge produce redundant first and second output voltages $V_{O1}$ and $V_{O2}$. The longitudinal distribution of the tension and compression gauge sensor resistors of the pair of interleaved split full-bridges of FIG. 3 and the pair of staggered split full-bridges of FIG. 5 cancels out and substantially removes noise that may be caused by forces from other sources such as off axis load moments in any of three directions and forces in either of the two orthogonal directions to the force being measured. Furthermore, each of the full-bridges of the pair of interleaved split full-bridges and each of the full-bridges of the pair of staggered split full-bridges includes both tension and compression strain gauge resistors configured to substantially cancel the effects of temperature variation. Moreover, the interleaving of these strain gauge resistors in the example of FIG. 3 ensures that they measure strain at the same locations of the beam, which ensures that the redundant first output voltage $V_{O1}$ and second output voltage $V_{O2}$ have matching values even if there are temperature variations along the length of the beam.

Thus, the distribution of gauge sensor resistors of each full-bridge between proximal and distal end portions of the beam removes the effects of noise resulting from other sources of force and cancel the effects of temperature so that the first and second output signals $V_{O1}$ and $V_{O2}$ produce the same redundant value. The first and second output signal values VO1 and $V_{O2}$ may be compared to determine whether they have different values. A determination that $V_{O1}$ and $V_{O2}$ have different values provides an indication of an error due to damage to the force sensor, for example.

Figure 6:
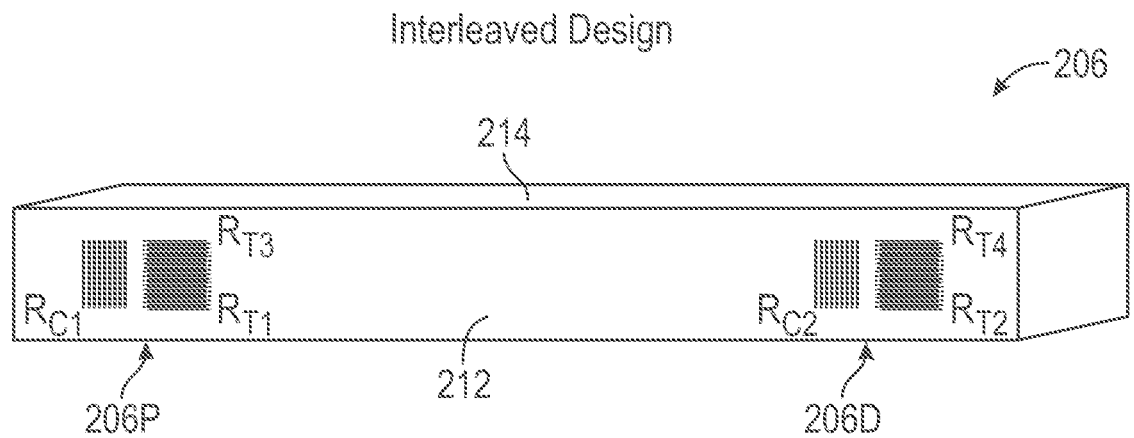
FIG. 6 is an illustrative perspective view of a force sensor beam having a beam face side with a pair of interleaved split half-bridge circuits.

FIG. 6 is an illustrative perspective view of a force sensor beam 206 having a beam face 212 with a pair of interleaved split half-Wheatstone bridges (half-bridges) each comprising tensile gauge sensor resistors formed at proximal and distal end portions of the beam 206 and having a shared half-bridge comprising compression gauge resistors formed at proximal and distal end portions of the beam, in accordance with some examples. A first tensile gauge half-bridge includes strain gauge resistor $R_{T1}$ at the proximal end portion 206P and includes strain gauge resistor $R_{T2}$ at the distal end portion 206D. A second tensile gauge half-bridge includes strain gauge resistor $R_{T3}$ at the proximal end portion 206P and includes strain gauge resistor $R_{T4}$ at the distal end portion 206D. The compression gauge half-bridge includes strain gauge resistor $R_{C1}$ at the proximal end portion and includes strain gauge resistor $R_{C2}$ at the distal end portion 206D. An identical pair of interleaved split half-bridges (not shown) comprising tensile gauge sensor resistors and an identical shared half-bridge (not shown) comprising compression gauge sensor resistors are formed on an adjacent orthogonal beam face 214. The pair of interleaved split half-bridges formed on adjacent orthogonal faces are configured to measure forces perpendicular to the longitudinal axis 210 of the beam 206, which may impart tensile strain to the beam. The shared compression gauge sensor resistors formed on adjacent orthogonal beam faces are configured to measure forces parallel to the longitudinal axis of the beam, which may impart compression strain to the beam 206.

Figure 7:
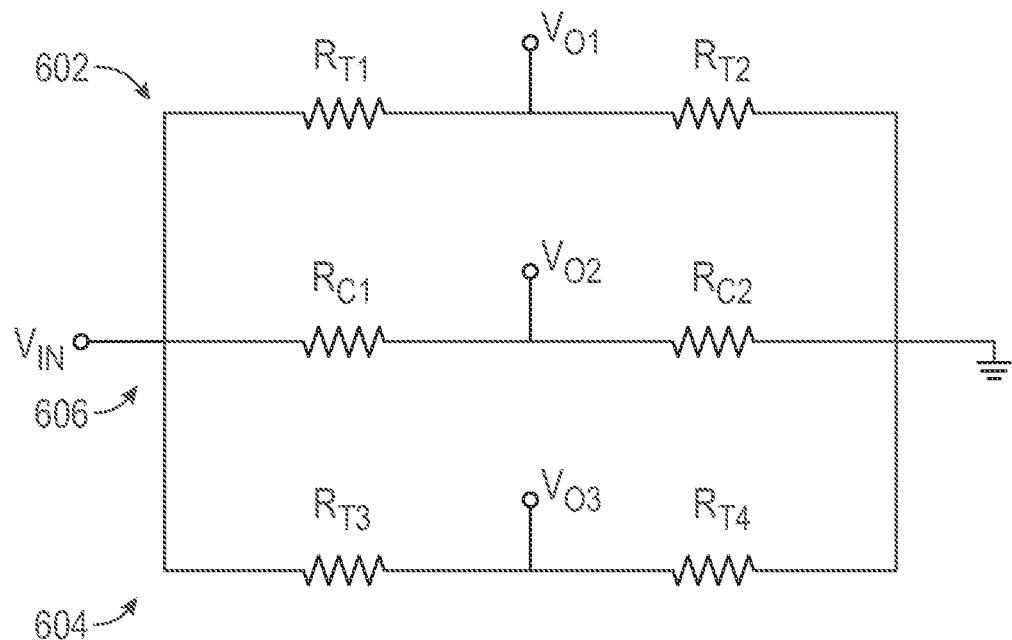
FIG. 7 is an illustrative schematic diagram representative of three half-bridge circuits.

FIG. 7 is an illustrative schematic diagram representative of three half-bridges. A first tension gauge half-bridge 602 includes tension strain gauge resistors $R_{T1}$ and $R_{T2}$ aligned along a neutral axis. A second tension gauge half-bridge 604 includes tension strain gauge resistors $R_{T3}$ and $R_{T4}$ aligned along a neutral axis. A compression half-bridge 606 includes compression strain gauge resistors $R_{C1}$ and $R_{C2}$ aligned along a neutral axis. Each of the first and second tension gauge half-bridges 602, 604 and the compression gauge half-bridge 606 is coupled to receive an input voltage $V_{in}$. The first tension gauge half-bridge 602 is coupled to provide a first tension force output $V_{O1}$. The second tension gauge half-bridge 604 is coupled to provide a second tension force output $V_{O3}$. The compression gauge half-bridge 606 is coupled to produce a compression force output $V_{O2}$. Each resistor $R_{T1}$-$R_{T4}$ and $R_{C1}$-$R_{C2}$ includes a plurality of parallel elongated portions aligned in parallel and coupled end-to-end to form a serpentine or snake-like configuration. The elongated portions of resistors $R_{C1}$-$R_{C2}$ are aligned perpendicular to the longitudinal axis 210 of the beam 206 to act as compression gauge sensors. The elongated portions of resistors $R_{T1}$-$R_{T4}$ are aligned parallel to the longitudinal axis 210 of the beam 206 to act as tension gauge sensors.

Referring again to FIG. 6, each interleaved split half-bridge has a tension gauge sensor resistor and a shared compression gauge sensor resistor disposed at the proximal end portion 206P of the beam 206. Each interleaved split half-bridge also has a tension gauge sensor and a shared compression gauge sensor disposed at the distal end portion 206D of the beam 206. Specifically, strain gauge resistors, $R_{T1}$, $R_{C1}$ and $R_{T3}$ are disposed at the proximal end portion 206P of the beam 206, and strain gauge resistors $R_{T2}$, $R_{C2}$ and $R_{T4}$ are disposed at the distal end portion 206D of the beam 206.

Figure 8:
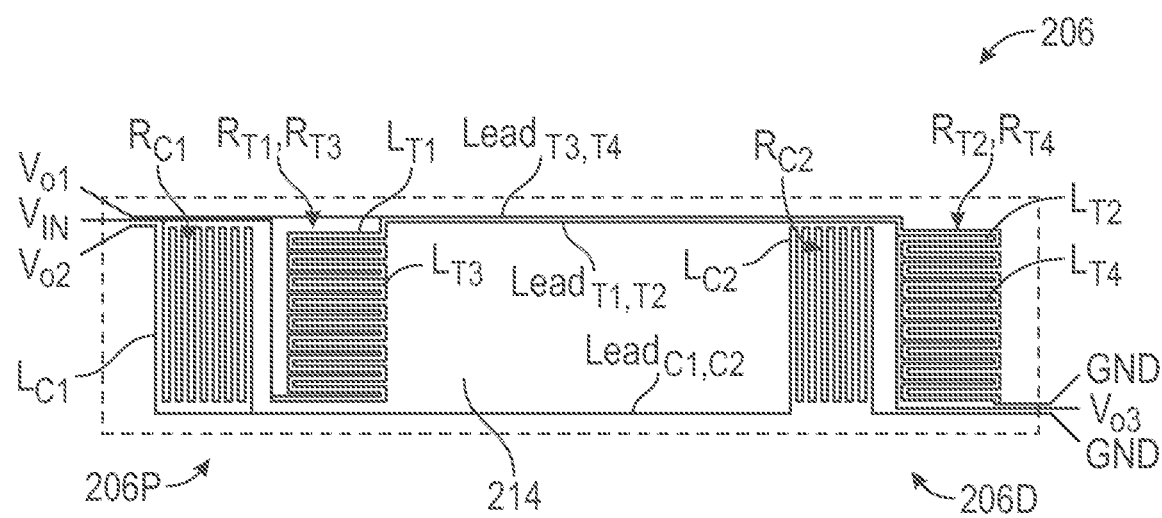
FIG. 8 is an illustrative side view of the beam showing arrangement of the gauge sensors of the interleaved three half-bridges example of FIG. 6.

FIG. 8 is an illustrative side view of the beam, indicated by dashed lines, representing arrangement of the gauge sensors of the interleaved three half-bridges example of FIG. 6. The elongated portions $L_{T1}$ of strain gauge resistor $R_{T1}$ are interleaved with elongated portions $L_{T3}$ of strain gauge resistor $R_{T3}$ so as to be co-located and occupy same longitudinal region of the beam. The interleaved strain gauge resistors $R_{T1}$ and $R_{T3}$ are farther from the proximal end of the beam than is the compression gauge resistor $R_{C1}$. $Lead_{T1,T2}$, which extends between the proximal and distal end portions, couples $R_{T1}$ located at the proximal end portion 206P with $R_{T2}$ located at the distal end portion 206D. Elongated portions $L_{T2}$ of strain gauge resistor $R_{T2}$ are interleaved with elongated portions $L_{T4}$ of strain gauge resistor $R_{T4}$ so as to be co-located and occupy same longitudinal region of the beam. The interleaved strain gauge resistors $R_{T2}$ and $R_{T4}$ are disposed closer to the distal end of the beam than is the compression gauge resistor $R_{C2}$. $Lead_{T3,T4}$, which extends between the proximal and distal end portions, couples $R_{T3}$ located at the proximal end portion 206P with $R_{T4}$ located at the distal end portion 206D. $Lead_{C1,C2}$, which extends between the proximal and distal end portions, couples Rc1 located at the proximal end portion 206P with $R_{c2}$ located at the distal end portion 206D.

Figure 9:
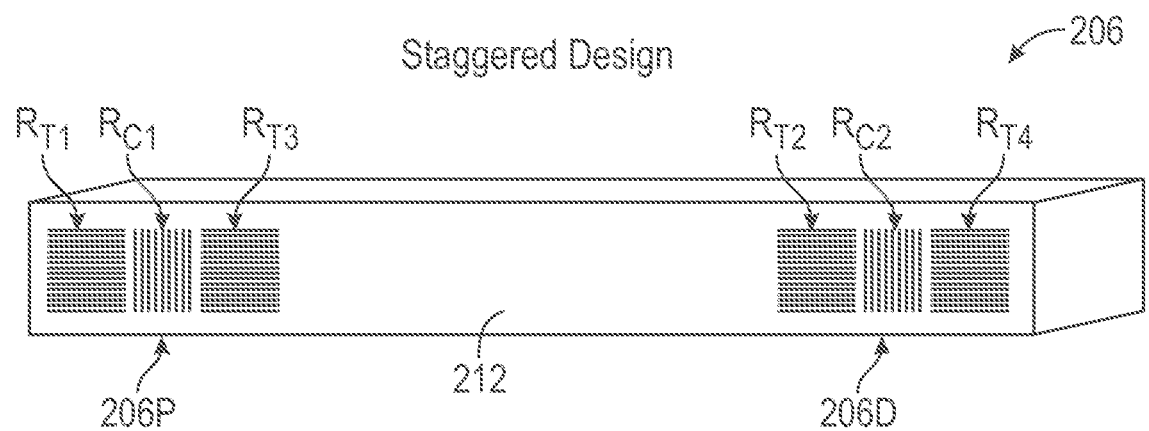
FIG. 9 is an illustrative perspective view of a force sensor beam having a beam face with a pair of staggered split half-bridge circuits.

FIG. 9 is an illustrative perspective view of a force sensor beam 206 having a beam face 212 with a pair of staggered split half-bridges each comprising tension gauge sensor resistors formed at proximal and distal end portions of the beam and having a shared half-bridge comprising compression gauge resistors formed at proximal and distal end portions of the beam, in accordance with some examples. The schematic diagram of FIG. 7 also is representative of staggered three half-bridges of FIG. 9. A first tensile gauge half-bridge includes strain gauge resistor $R_{T1}$ at the proximal end portion 206P and includes strain gauge resistor $R_{T2}$ at the distal end portion 206D. A second tensile gauge half-bridge includes strain gauge resistor $R_{T3}$ at the proximal end portion 206P and includes strain gauge resistor $R_{T4}$ at the distal end portion 206D. The compression gauge half-bridge includes strain gauge resistor $R_{C1}$ at the proximal end portion and includes strain gauge resistor $R_{C2}$ at the distal end portion 206D. An identical pair of interleaved split half-bridges (not shown) comprising tensile gauge sensor resistors and an identical shared half-bridge (not shown) comprising compression gauge sensor resistors are formed on an adjacent orthogonal beam face 214. The pair of interleaved split half-bridges formed on adjacent orthogonal faces are configured to measure forces perpendicular to the longitudinal axis 210 of the beam 206, which may impart tensile strain to the beam 206. The shared compression gauge sensor resistors formed on adjacent orthogonal beam faces are configured to measure forces parallel to the longitudinal axis 210 of the beam, which may impart compression strain to the beam 206.

Figure 10:
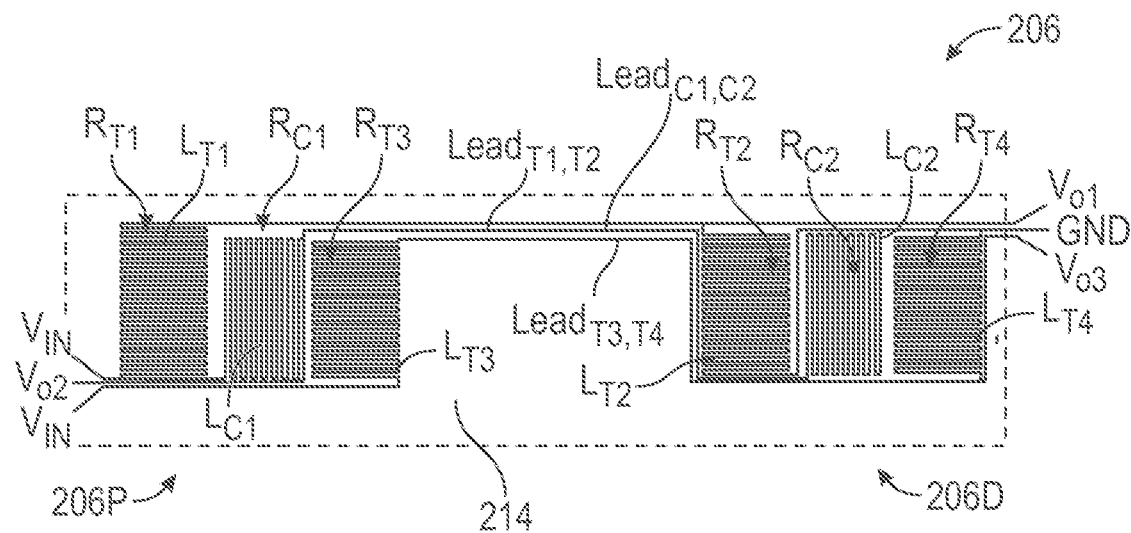
FIG. 10 is an illustrative side view representing arrangement of the gauge sensors of the staggered three half-bridges example of FIG. 9.

FIG. 10 is an illustrative side view representing arrangement of the gauge sensors of the staggered three half-bridges example of FIG. 9. A first tension gauge resistor half-bridge includes tension strain gauge resistors, $R_{T1}$ and $R_{T2}$ aligned along a neutral axis. A second tension gauge resistor half-bridge includes tension strain gauge resistors, $R_{T3}$ and $R_{T4}$ aligned along a neutral axis. A compression gauge resistor half-bridge includes compression strain gauge resistors $R_{C1}$ and $R_{C2}$ aligned along a neutral axis. A first compression gauge resistor Rei is disposed at a proximal end portion of the beam between first and third tension gauge resistors $R_{T1}$, $R_{T3}$, with the first tension gauge resistor $R_{T1}$ disposed closer to the proximal end of the beam than the third tension gauge resistor $R_{T3}$. A second compression gauge resistor $R_{C2}$ is disposed at a distal end portion of the beam between second and fourth tension gauge resistors $R_{T2}$, $R_{T4}$, with the fourth tension gauge resistor $R_{T4}$ disposed closer to the distal end of the beam than the second tension gauge resistor $R_{T2}$. $Lead_{T1,T2}$, which extends between the proximal and distal end portions, couples $R_{T1}$ located at the proximal end portion 206P with $R_{T2}$ located at the distal end portion 206D. $Lead_{T3,T4}$, which extends between the proximal and distal end portions, couples $R_{T3}$ located at the proximal end portion 206P with $R_{T4}$ located at the distal end portion 206D. $Lead_{C1,C2}$, which extends between the proximal and distal end portions, couples $R_{C1}$ located at the proximal end portion 206P with $R_{c2}$ located at the distal end portion 206D.

Thus, both the interleaved split half-bridge and the staggered split half-bridge produce redundant first and second tension force output voltages $V_{O1}$ and $V_{O3}$. The longitudinal distribution of the tension and compression gauge sensor resistors of the pair of interleaved split half-bridges of FIG. 6 and the pair of staggered split half-bridges of FIG. 9 cancels out and substantially removes noise that may be caused by forces from other sources such as off axis load moments in any of three directions and forces in either of the two orthogonal directions to the force being measured. Moreover, in the interleaved half-bridges example of FIG. 6, the interleaving of the strain gauge resistors ensures that they measure strain at the same locations of the beam, which ensures that the redundant first output voltage $V_{O1}$ and third output voltage $V_{O3}$ have matching values even if there are temperature variations along the length of the beam.

In arriving at this invention, the inventor realized that each half-bridge (both tension gauge half-bridges and compression gauge half-bridge) cancels the following stresses: moment, off axis force, off axis moment, compression/tension, torsion, and ambient temperature. The inventor also realized that each individual half-bridge output includes the following: force and gradient temperature. The inventor further realized that if Vo is the output of the half bridge $$V_o = GF * \frac{V_{in}}{4}(\epsilon_p - \epsilon_d)$$

Where $\epsilon_p$ and $\epsilon_d$ represent the proximate stress and the distal stress and GF represents the gauge factor.

Then subtraction in $(\epsilon_p - \epsilon_d)$ in the above equation cancels: moment, off axis force, off axis moment, compression/tension, torsion, and ambient temperature, Now subtracting the 'T gauge' half-bridge output and 'C gauge' half-bridge output, we cancel the following: gradient temperature.

If Vo1 is the output of the half-bridges of 'T gauges' and Vo2 is the output of the half-bridge of 'C gauges', then the subtraction in Vo1−Vo2 cancels ambient temperature and gradient temperature and the final output after subtraction is only the sought after 'Force'

For the split half-bridge examples of FIG. 6 and FIG. 9, redundant comparisons may be performed as follows.

The redundant comparison is done after extracting the force signal and temperature differential signal from the half-bridge measurements $V_{O1}$, $V_{O2}$ and $V_{O3}$.

For X axis, for example, (indicated by 'x')
We can use $V_{O1\_x}$ and $V_{O2\_x}$ to get Force1_x and deltaT1_x
We can use $V_{O3\_x}$ & $V_{O2\_x}$ to get Force2_x and deltaT2_x
For Y axis (indicated by 'y')
We can use $V_{O1\_y}$ & $V_{O2\_y}$ to get Force1_y and deltaT1_y
We can use $V_{O2\_y}$ & $V_{O2\_y}$ to get Force2_y and deltaT2_y
For redundancy check
Force_x: we check whether Force1_x and Force2_x match
Force_y: we check whether Force1_y and Force2_y match
deltaT: we check whether deltaT1_x and deltaT1_y match
These comparison checks will cover failures in any of the gauges.
deltaT2_x and deltaT2_y are kind of throw away terms because they don't provide additional information.
The math used to compute force and deltaT from voltage output is as follows $$F_\| = \frac{T \text{ gauge } V_o - C \text{ gauge } V_o}{(1+\rho_r)K_f} \text{ where } K_f = \frac{1}{4}GFV_{in}r\frac{l_1 - l_2}{E1}$$

-continued
$$\Delta T = \frac{C \text{ gauge } V_o + \rho_r(T \text{ gauge } V_o)}{(1+\rho_r)K_T} \text{ where } K_T = \frac{1}{4}GFV_{in}CTE$$

Where 'T gauge Vo' is $V_{O1}$ and 'C gauge Vo' is $V_{O2}$.

Thus, the distribution of gauge sensor resistors of each tension gauge half-bridge between proximal and distal end portions of the beam removes the effects of noise resulting from other sources of force and cancel the effects of temperature so that the first and second tension gauge force output signals $V_{O1}$ and $V_{O3}$ produce the same redundant value. The first and second tension gauge force output signal values $V_{O1}$ and $V_{O3}$ may be compared to determine whether they have different values. A determination that $V_{O1}$ and $V_{O3}$ have different values provides an indication of an error due to damage to the force sensor, for example.

Figure 11:
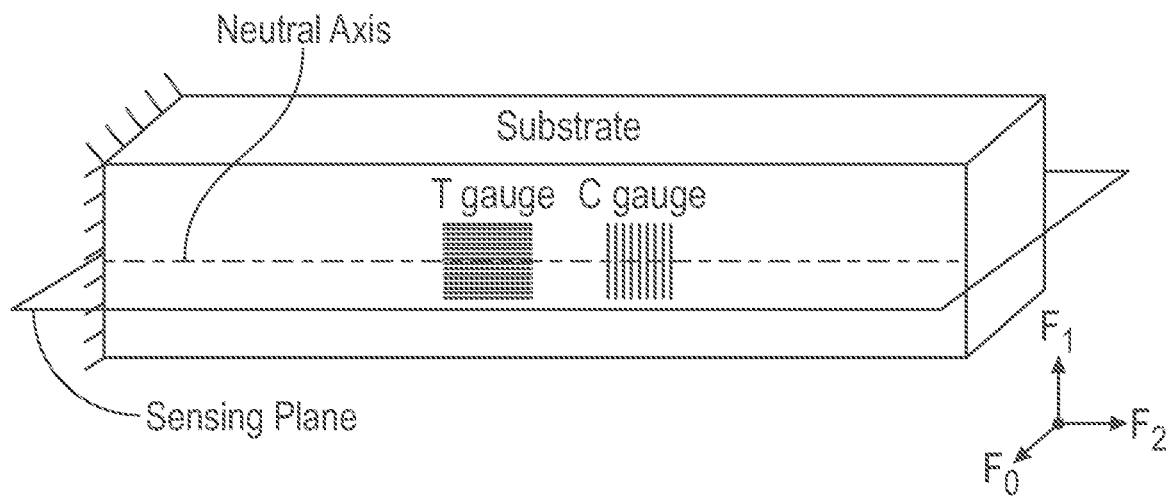
FIG. 11 is an illustrative perspective view of a beam with a T-gauge (tension) and C gauge (compression) disposed along a neutral axis of a beam.

Redundant temperature values are provided by the compression output values $V_{O2}$ produced by the compression gauge half-bridges formed adjacent orthogonal faces. The compression output values $V_{O2}$ produced by the half-bridges formed adjacent orthogonal faces may be compared to determine whether they have different values. A determination that the compression gauge half-bridges on adjacent orthogonal faces have different values provides an indication of an error due to damage to the force sensor, for example.
Proof
A. Determining T-Gauge Strain and C-Gauge Strain:

FIG. 11 is an illustrative perspective view of a beam with a T-gauge (tension) and C gauge (compression) disposed along a neutral axis of a beam.

Values used to determine force and change in temperature include:
$F_g$: Force along the sensing plane
l: Location of the force applied
M: Moment applied perpendicular to the sensing plane
$F_z$: Force applied parallel to the neutral axis
I: Moment of inertia
A: Area or cross section
CTE: Coefficient of thermal expansion
ΔT: Change in temperature
ε: Strain
ρ: Poisson's ratio
T-gauge strain measurement equation:

$$\epsilon = -\frac{F_g l r}{E1} + \frac{M_\perp r}{E1} - \frac{F_2}{EA} + CTE.\Delta T$$

C gauge strain measurement equation:

$$\epsilon = -pr\left(-\frac{F_g l r}{E1} + \frac{M_\perp r}{E1} - \frac{F_2}{EA}\right) + CTE.\Delta T$$

Figure 12:
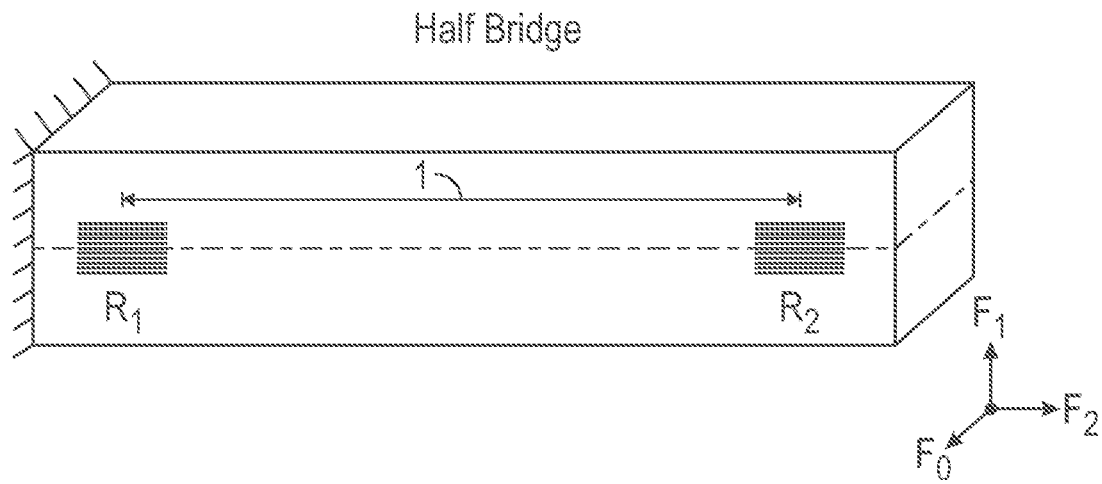
FIG. 12 is an illustrative perspective view of a beam with tension gauges R1 and R2 disposed along a neutral axis of a beam, respectively, at a proximal end portion and at a distal end portion of the beam.
Figure 13:
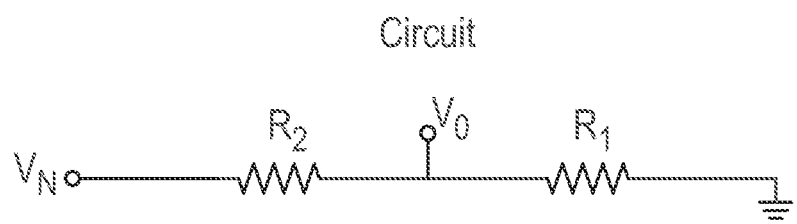
FIG. 13 is an illustrative schematic diagram representing a half-bridge circuit containing R1 and R2 of FIG. 12.

B. Determining Force and ΔT:

FIG. 12 is an illustrative perspective view of a beam with tension gauges R1 and R2 disposed along a neutral axis of a beam, respectively, at a proximal end portion and at a distal end portion of the beam. FIG. 13 is an illustrative schematic diagram representing a half-bridge circuit containing R1 and R2 of FIG. 12.

For the half-bridge of FIGS. 12-13, using the above T-gauge strain measurement, we can calculate $V_o$ based upon R1, R2 and $V_{in}$ $$V_o = \frac{R2}{R1+R2} * V_{in}$$

$$R_i = R + \Delta R_i \text{ where } i = 1,2$$

$$\Delta R_i = GF * \epsilon_i$$

The nominal resistance of both gauges is the same R value under no load. The change in resistance dependence on strain experienced by the gauge times the gauge factor. For small resistance change, using first order approximation we get the following equation.

$$V_o = \frac{1}{2} + \frac{1}{4}(\epsilon_2 - \epsilon_1) * GF * V_{in}$$

We can substitute the strain equation to get $V_o$ in terms of force.

$$T \text{ gauge } V_o = \frac{1}{2} + \frac{1}{4}\left(F_\parallel r \frac{(l_1 - l_2)}{EI} + CTE(\Delta T_2 - \Delta T_1)\right) * GF * V_{in}$$

Similarly, we get an equation for the half-bridge using the compression (C) gauges.

$$C \text{ gauge } V_o = \frac{1}{2} + \frac{1}{4}\left(-\rho_r F_\parallel r \frac{(l_1 - l_2)}{EI} + CTE(\Delta T_2 - \Delta T_1)\right) * GF * V_{in}$$

With equations for C gauge and T gauge, we can solve for $F_{11}$ and $\Delta T = (\Delta T_1 - \Delta T_2)$, we get, $$F_\parallel = \frac{T \text{ gauge } V_o - C \text{ gauge } V_o}{(1 + \rho_r)K_f}$$

$$\text{where } K_f = \frac{1}{4}GFV_{in}r\frac{l_1 - l_2}{EI}$$

$$\Delta T = \frac{C \text{ gauge } V_o + \rho_r (T \text{ gauge } V_o)}{(1 + \rho_r)K_r}$$

$$\text{where } K_r = \frac{1}{4}GFV_{in}CTE$$

Figure 14:
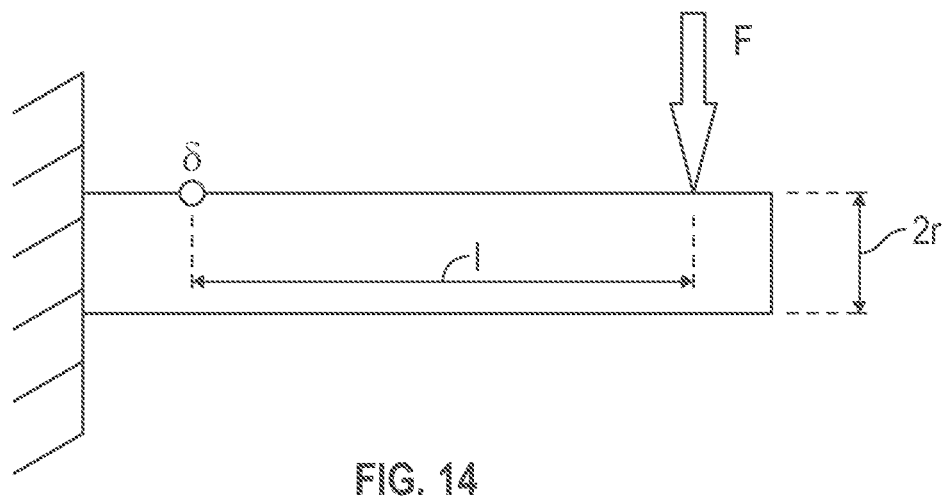
FIG. 14 is an illustrative side view of a force applied to a cantilever beam indicating strain measurement at a distance 1 from the location where force is applied to the beam.

C. Basic Force Measurement Using Strain:

FIG. 14 is an illustrative side view of a force applied to a cantilever beam indicating strain measurement at a distance l from the location where force is applied to the beam. Strain Equation for a perpendicular force applied on distal end a Cantilever Beam is
Where $$\epsilon = \frac{Flr}{EI}$$

E: Modulus of elasticity
I: Moment of inertia

We can see that the strain equation depends on the force 'F' applied as well as the distance 'l' from the sensing point. Therefore, to be able to measure the Force applied we need a second measurement to eliminate the dependence of 'l'. The most obvious way to do this is to measure the strain at different point along the beam.

Figure 15:
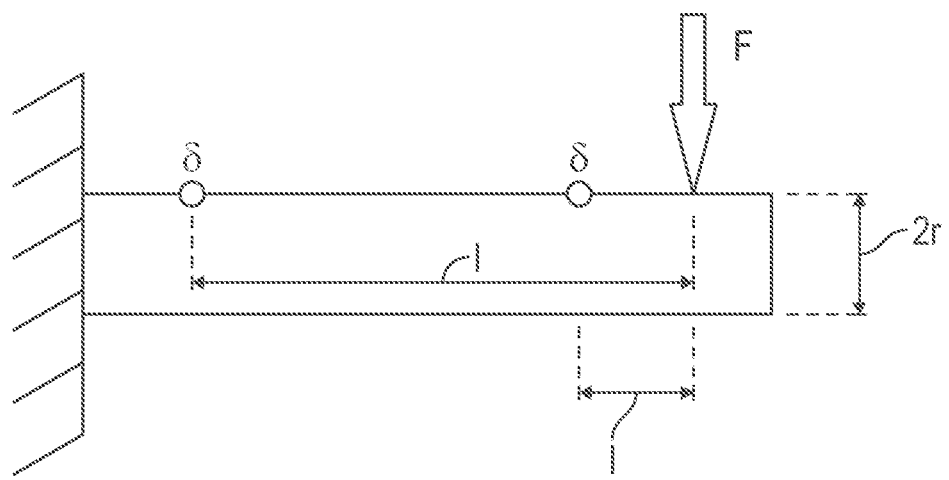
FIG. 15 is an illustrative side view of a force applied to a cantilever beam indicating strain measurement at a proximal distance and at a distal distance from the location where force is applied to the beam.

FIG. 15 is an illustrative side view of a force applied to a cantilever beam indicating strain measurement at a proximal distance lprox and at a distal distance ldist from the location where force is applied to the beam. Then we get $$\epsilon_{prox} = \frac{Fl_{prox}r}{EI}$$

$$\epsilon_{dist} = \frac{Fl_{dist}r}{EI}$$

Then when we subtract the 2 measurements we get $$\epsilon_{prox} - \epsilon_{dist} = \frac{Fr}{EI}(l_{prox} - l_{dist})$$

The difference in distance is a known quantity; it is the distance between the two sensing points.

D. Force Measurements Under Noise Sources

Figure 16:
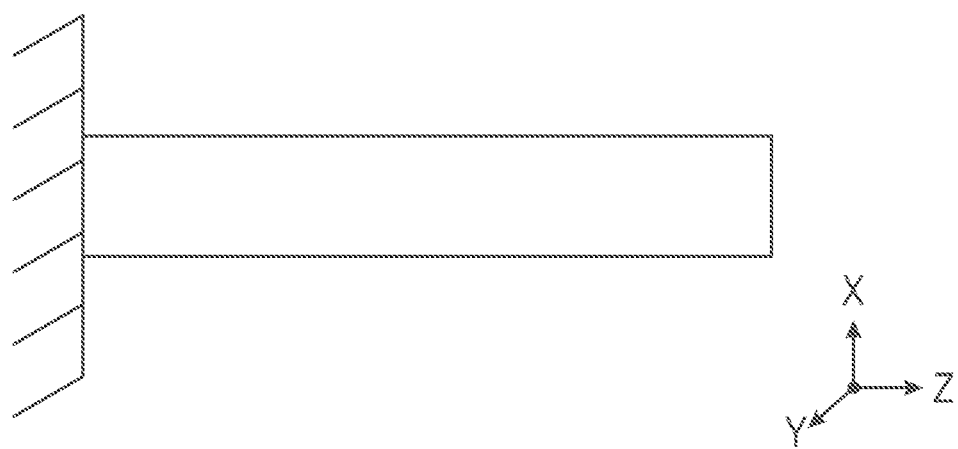
FIG. 16 is a side view of a cantilever beam.

FIG. 16 is a side view of a cantilever beam.

In typical force measurement scenario there is presence of noise sources/signals that are of no interest to us but still produce a measurable strain on the beam, which we are sensing and this will result in incorrect estimation of the force applied. Some other sources of strain that could be present are Force in the 2 orthogonal directions
Moments in all 3 directions
Temperature changes If the reference frame is selected such that the Force we want to measure is oriented along X axis then, the unwanted strain sources for measuring are, Forces (Fy, Fz), Moments (Mx, My, Mz) and Temperature ($\Delta T$)

Therefore, the most general strain equation for a point sensing element on the cantilever beam oriented parallel to neutral axis is as follows $$T \text{ gauge strain} = \epsilon_t = -\frac{F_x lr}{EI} - \frac{F_y r}{EI} + \frac{F_z}{EA} - \frac{M_y r}{EI} + \frac{M_x d}{EI} + \epsilon_{t_{M_z}} + CTE * \Delta T$$

$$C \text{ gauge strain} = \epsilon_c = -\rho_r\left(-\frac{F_x lr}{EI} - \frac{F_y r}{EI} + \frac{F_z}{EA} - \frac{M_y r}{EI} + \frac{M_x d}{EI} + \epsilon_{c_{M_z}} + CTE * \Delta T\right)$$

Where
- E: Modulus of elasticity
- I: Moment of inertia
- r: Perpendicular distance to YZ plane passing through the neutral axis
- d: Perpendicular distance to XZ plane passing through the neutral axis
- A: Area of cross section
- CTE: Coefficient of thermal expansion
- $\epsilon_{C_{Mz}}$: Strain due to torsion Mz perpendicular to neutral axis
- $\epsilon_{t_{Mz}}$: Strain due to torsion Mz parallel to neutral axis
- $\rho_r$: poisson ratio of the substrate As can be see from the equation above, a point measurement of strain will be dependent on lot of strain sources. The act of subtracting the proximal and distal measurements will also eliminate some sources of strain as common mode. The following gets eliminated
- Force: Fz
- Moments: My, Mz If the sensing point/element is placed symmetrically about the neutral axis (d=0), then the following does not affect the strain measurement
- Force: Fy
- Moment: Mx Therefore the strain source that is not compensated is temperature change. The most trivial way to compensate for temperature is to use Wheatstone bridge configuration using 'C' (compression) and 'T' (tension) gauges to locally eliminate strain from temperature change.

Figure 17A:
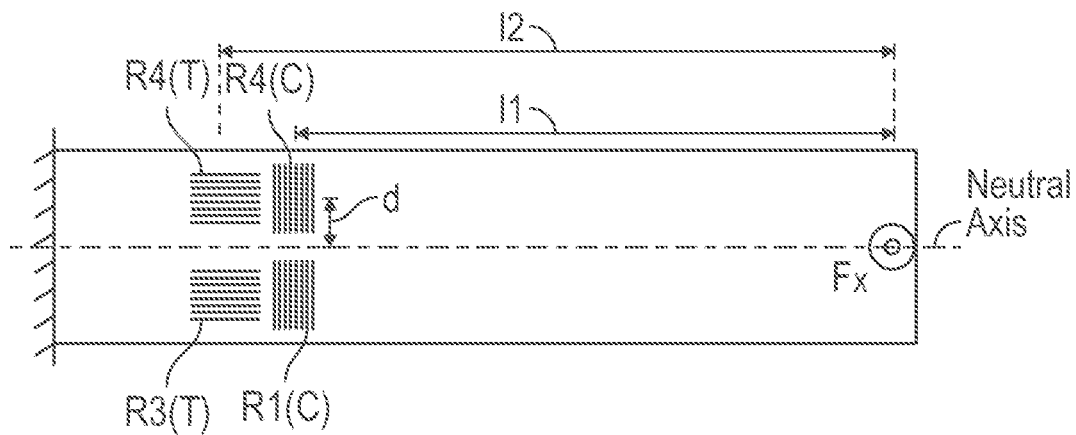
FIG. 17A is a side view of a beam with a Wheatstone bridge disposed at a proximal end thereof.
Figure 17B:
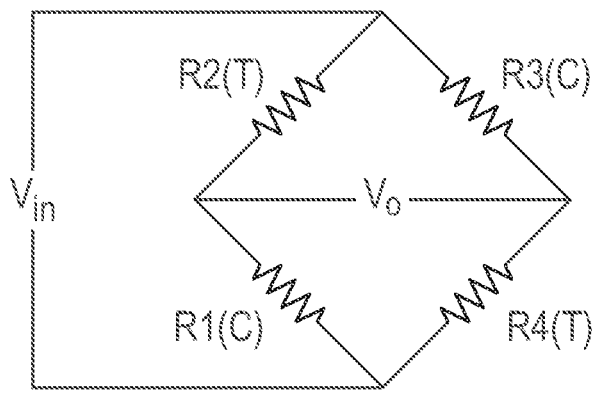
FIG. 17B is a schematic diagram of the Wheatstone bridge circuit of FIG. 17A.

FIG. 17A is a side view of a beam with a Wheatstone bridge disposed at a proximal end thereof. FIG. 17B is a schematic diagram of the Wheatstone bridge circuit of FIG. 17A.

The output of the Wheatstone bridge is as follows $$V_{out} = \left(\frac{R_1}{R_1 + R_2} - \frac{R_4}{R_3 + R_4}\right)V_{in}$$

The resistance strain relationship of gauges is as follows $$R = R_o + GF * \epsilon * R_o$$

If the nominal resistance of all the gauges are same and if substitute the strain—resistance relationship and perform a first order approximation we get the following equation $$V_{out} = GF * \frac{V_{in}}{4}(\epsilon_2 - \epsilon_1 - (\epsilon_3 - \epsilon_4))$$

When Fx is applied, the above equation reduces to the form $$V_{out} = K * F * l$$

Where K is a scalar constant and $l = \Delta l + (1 + \rho_r)l_1$ and $\Delta l = l_2 - l_1$ So, we get output signal proportional to applied force When there is a temperature change then the strain seen by all gauges are same and the output ends up being zero, which implies temperature changes are compensated locally.

Therefore, to measure the applied force in the sensing direction (x axis) we need two Wheatstone bridge located near the proximal and distal end of the beam.

E. Measuring Force Using a Single Wheatstone Bridge

Figure 18:
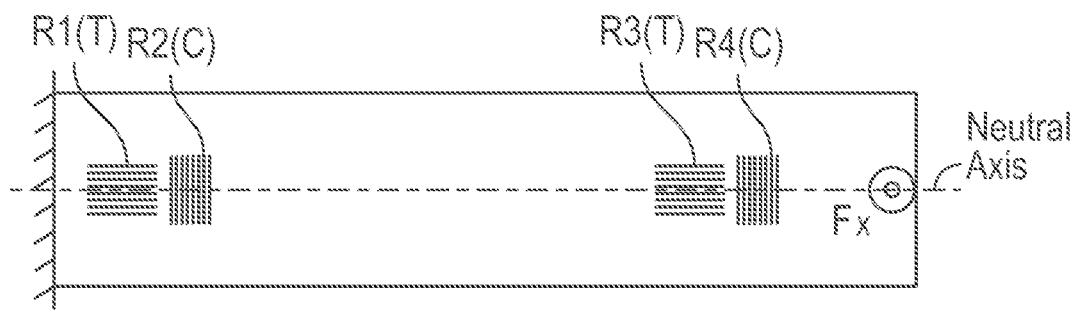
FIG. 18 is a side view of a beam with a split Wheatstone bridge having a tension gauge resistor R1 and a compression gauge resistor R2.

FIG. 18 is a side view of a beam with a split Wheatstone bridge having a tension gauge resistor R1 and a compression gauge resistor R2 disposed along a neutral axis at a proximal end portion thereof and having a tension gauge resistor R3 and a compression gauge resistor R4 disposed along a neutral axis at a distal end portion thereof. The schematic diagram of FIG. 17B is applicable to the split bridge of FIG. 18.

If we look at the trivial design we locally compensate for temperature, then measure two signals and externally subtract the two signals to get Force applied, but the structure of Wheatstone bridge equation has the ability subtract signals internally, so we can use this to our advantage. Also, we can arrange the gauges such that instead of temperature being compensated locally we can compensate temperature effect globally.

The temperature change seen at each measuring point can be decomposed into ambient temperature change which is same everywhere and temperature difference which is temperature delta between the ambient temperature and the temperature at the point. The ambient temperature change ends up being a common mode and just the act of subtracting the proximal and distal signal eliminates its effects.

In the above configuration, we get the output signal as $$V_{out} = GF * \frac{V_{in}}{4}((\epsilon_1 - \epsilon_2) - (\epsilon_3 - \epsilon_4))$$

If there was not temperature difference then we can see that R1 and R2 together can measure force applied and similarly R3 and R4 can measure the force applied, since R1, R2 is Tension gauge and R3,R4 is compression gauge their relationship with force applied varies by $-\rho_r$. Therefore, the total equation will reduce to $$V_{out} = GF * \frac{V_{in}}{4}(K * F_x - (-\rho_r K * F_x))$$

Where K is a fixed constant $$V_{out} = GF * \frac{V_{in}}{4} * K * (1 + \rho_r)F_x$$

The same configuration for temperature difference has different result, R1 and R2 measure the effect of temperature difference between the proximal and distal gauges, similarly R3 and R4 measure the effect of temperature difference. Even though the two pairs are different gauge types, they have the same sensitivity to strain due to temperature changes $$V_{out} = GF * \frac{V_{in}}{4}(K * \Delta T - (K * \Delta T))$$

Where K is a fixed constant $V_{out} = 0$

So, we can roughly consider the 'C' gauges as temperature compensation gauges and 'T' gauges as the measurement gauges.

Figure 19:
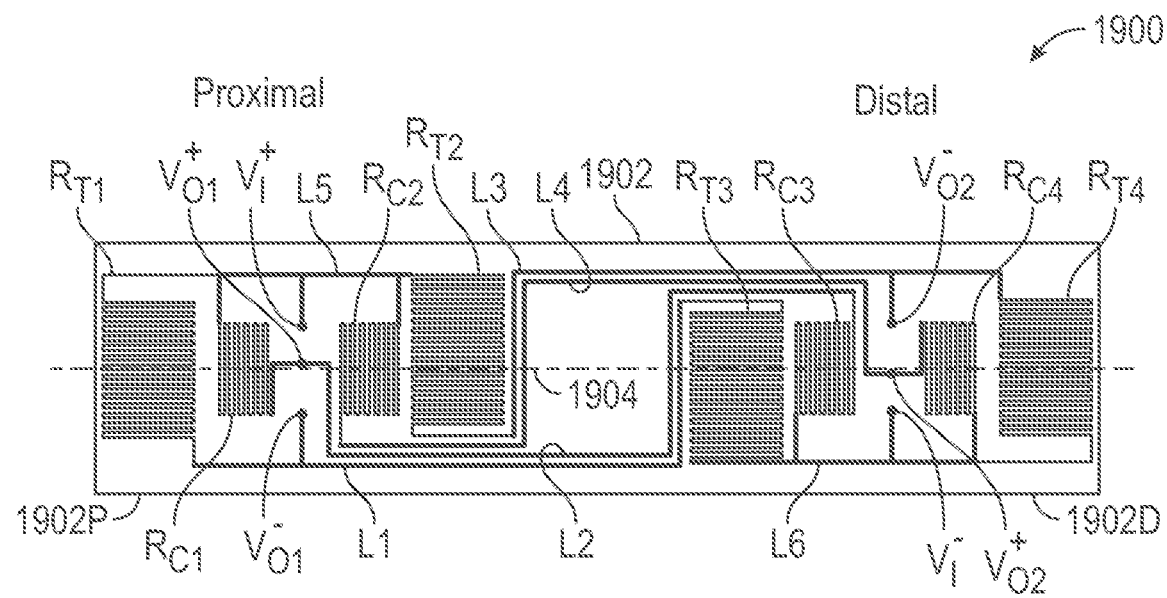
FIG. 19 is an illustrative drawing representing an example force sensor that includes a beam with two split full bridge circuits thereon.

FIG. 19 is an illustrative drawing representing a force sensor 1900 that includes a beam 1902 with two split full bridge circuits thereon. The beam 1902 includes a proximal end portion 1902P and a distal end portion 1902D and a center portion therebetween. A first split bridge circuit includes strain gauge resistors $R_{C1}$, $R_{C3}$, $R_{T1}$, $R_{T3}$. The first bridge circuit is split, with compression strain gauge resistor $R_{C1}$ and tension gauge resistor $R_{T1}$ located at a proximal end portion of the beam and compression strain gauge resistor $R_{C3}$ and tension gauge resistor $R_{T3}$ located at a distal end portion of the beam, $R_{T3}$. A second split bridge circuit includes strain gauge resistors $R_{C2}$, $R_{C4}$, $R_{T2}$, $R_{T4}$. The second bridge circuit is split, with compression strain gauge resistor $R_{C2}$ and tension gauge resistor $R_{T2}$ located at a proximal end portion of the beam and compression strain gauge resistor $R_{C4}$ and tension gauge resistor $R_{T4}$ located at a distal end portion of the beam.

Electrically conductive measurement output lead lines L1-L4 and input signal lead lines L5-L6 disposed upon the beam, electrically couple the strain gauge resistors as shown. Measurement output lead line L1 is disposed to extend integral with the proximal, center and distal portions of the beam to electrically couple $R_{T1}$ and $R_{T3}$ at a node VO1−. Measurement output lead line L2 is disposed to extend integral with the proximal, center and distal portions of the beam to electrically couple RC1 and RC3 at a node VO1+. Measurement output lead line L3 is disposed to extend integral with the beam to electrically couple RC2 and RC4 at a node VO2+. Measurement output lead line L4 is disposed to extend integral with the beam to electrically couple RT2 and RT4 at a node VO2−. Input signal lead line L5 extends within the proximal portion of the beam to electrically couple RC1, RC2, RT1 and RT2 at a node VI+. Input signal lead line L6 extends within the distal portion of the beam to electrically couple RC3, RC4, RT3 and RT4 at a node VI−. The lead lines L1-L6 are disposed integral with and mechanically coupled to the beam.

Input tap nodes VI+, coupled to RT1, RT3, RC1, RC3, and VI−, coupled to RT2, RT4, RC2, RC4 act as input signal nodes that are coupled to receive positive and negative polarities of an input excitation signal. Measurement tap nodes VO1− and VO1+ at the respective junction of RT1, RT3 and the junction of RC1, RC3, act as output measurement signal nodes that are coupled to provide output measurement signals indicative of strain. Likewise, measurement tap nodes VO2− and VO2+ at the respective junction of RT2, RT4 and the junction of RC2, RC4, act as output measurement signal nodes that are coupled to provide output measurement signals indicative of strain.

Figure 1:
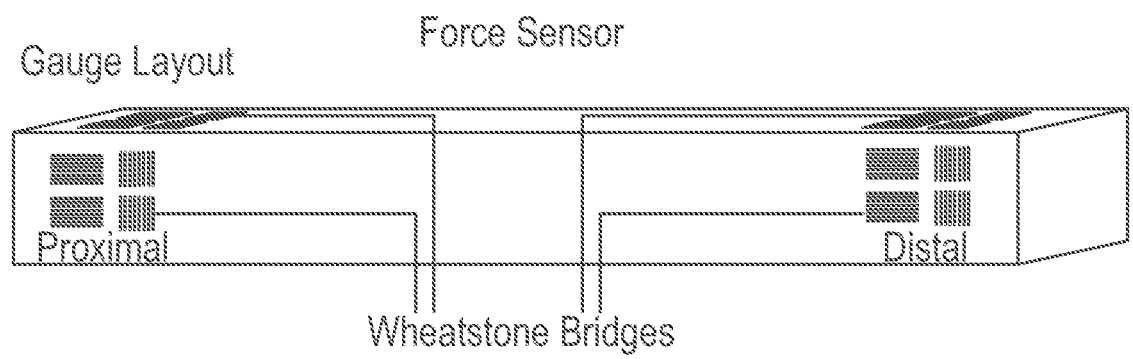
FIG. 1 is an illustrative drawing representing a force sensor that includes a rectangular beam with four full-Wheatstone bridges (full-bridges).

Since each split bridge includes both strain gauge resistors disposed at a proximal end portion of the beam and strain gauge resistors disposed at a distal end portion of the beam, the lead lines L1-L6 that electrically couple the resistors of each bridge are relatively long. For example, lead lines that couple the resistors of the first and second split bridges of FIG. 19 are relatively longer than lead lines used to couple resistors of the non-split bridge circuits of the illustrative bridge of FIG. 1 in which each bridge is located either entirely at a proximal end portion of the beam or at a distal end portion of the beam.

A split bridge circuit can introduce undesirable amounts of unbalanced lead resistance between the strain gauges because the gauges are distributed at beam location across large distances relative to the size of the strain gauges. The lead resistance can affect the accuracy of the sensor measurements and introduce cross coupling and temperature dependent offset.

More particularly the conductive lead lines are integrally formed upon the beam through deposition and etching process that produce the strain gauges. Preferably, the lead lines do not change electrical properties in response to forces imparted to a beam or to a change in temperature, for example. However, the conductive lead lines extending along the beam to couple the active resistive strain gauges at opposite end portions of the beam are subjected to strain as the beam deflects in response to force imparted to the beam, which changes the resistance of the conductive lines. In some examples, the length of the lead lines may be comparable in magnitude to the overall length of the conductor line portions that make up the of the serpentine-shaped resistive strain gauge elements. A change in resistance of the electrical conduction lines can result in distortion of strain measurements since the electrical connection lines are not intended as behave as active resistive elements of the bridge circuits. Thus, there is a need to reduce lead resistances and balances what minimal lead resistance remains left over.

Figure 20A:
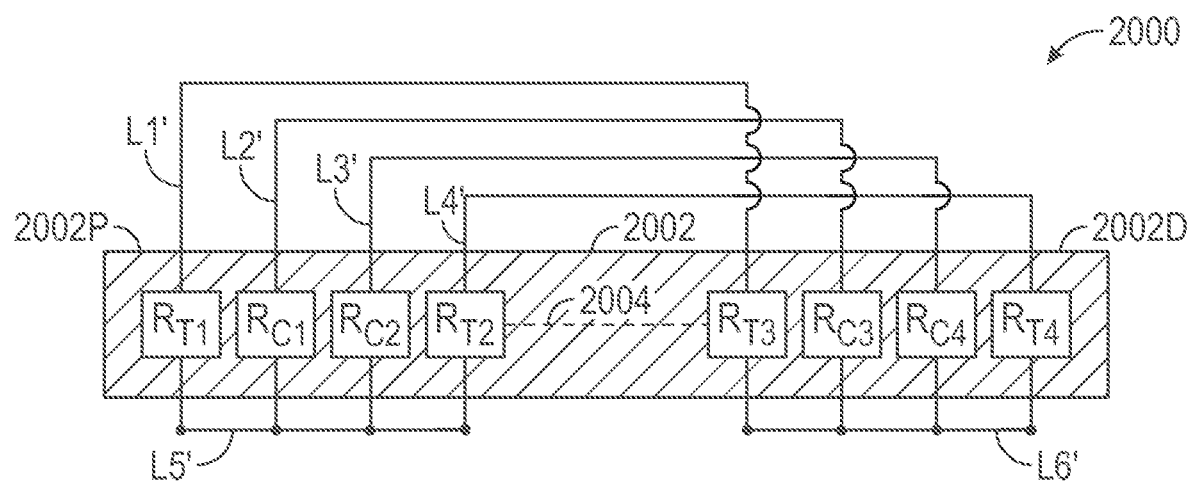
FIG. 20A is an illustrative simplified block diagram showing mechanically isolated lead lines extending between strain gauge elements of two proximal split bridge circuit halves and strain gauge elements of two distal split bridge circuit halves.
Figure 20B:
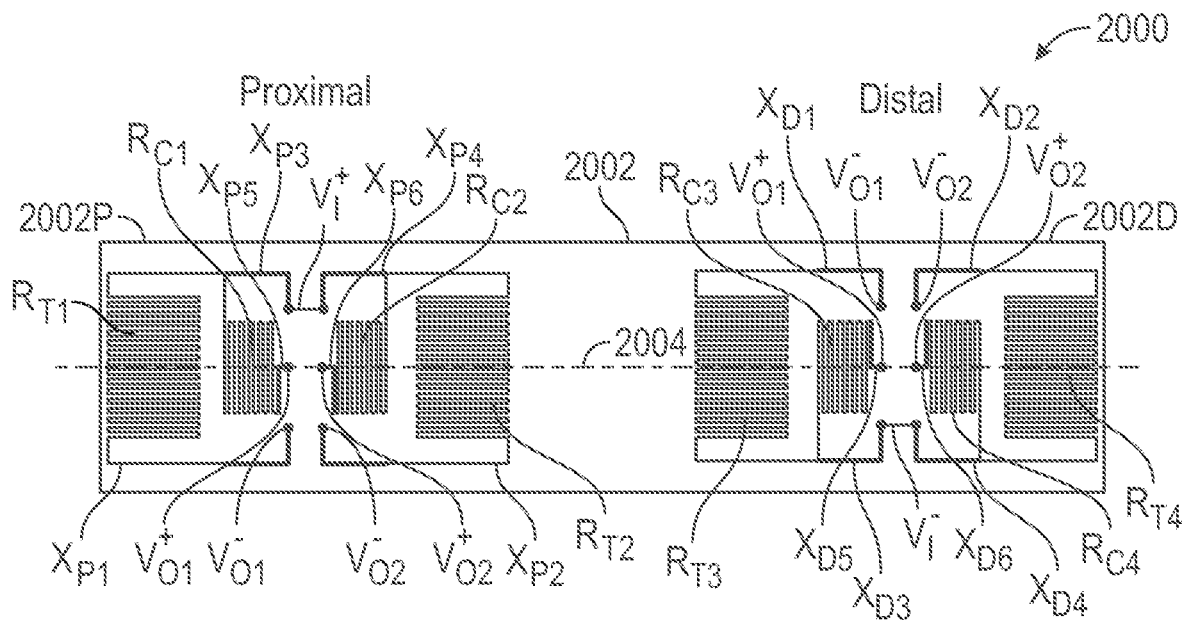
FIG. 20B is an illustrative drawing showing certain details of a first example arrangement of the strain gauge elements of the example sensor of FIG. 20A.
Figure 20C:
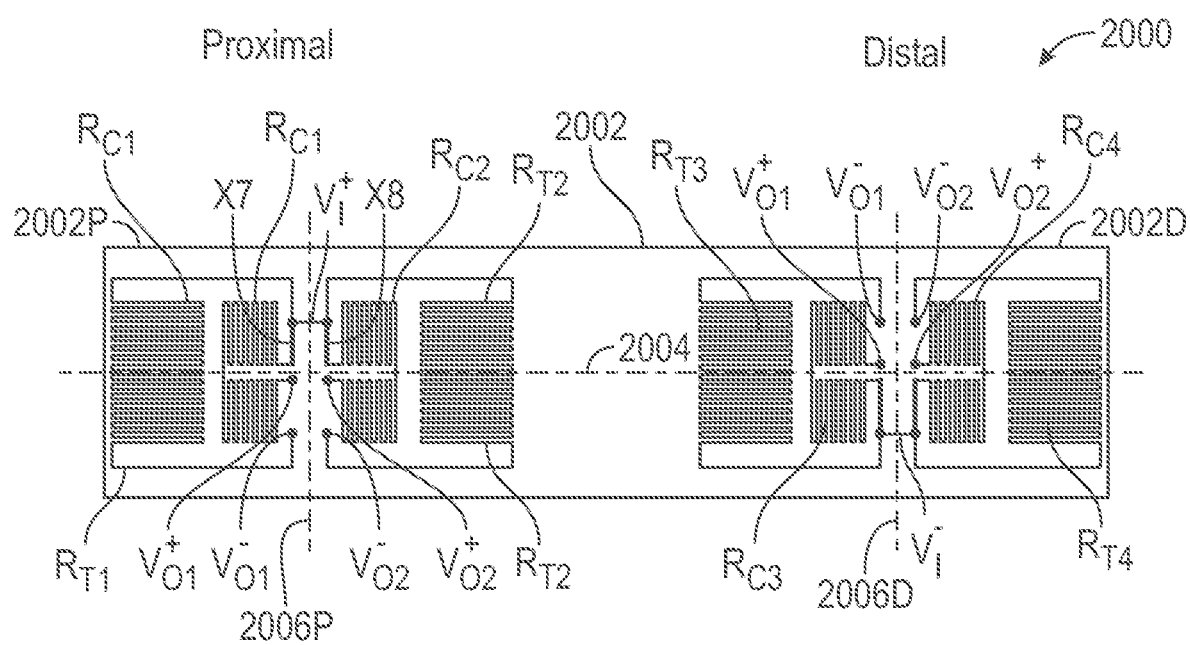
FIG. 20C is an illustrative drawing showing certain details of a second example arrangement of the strain gauge elements of the example sensor of FIG. 20A.

FIG. 20A-20B are is illustrative drawing representing an example force sensor 2000 that includes a beam 2002 having a neutral axis 2004 and that includes two split full bridge circuits with split bridge halves eclectically coupled by measurement output lead lines L1'-L4' and electrically coupled input lead lines L5-L6 are mechanically isolated from the beam 2002. FIG. 20A illustrates the strain gauge elements $R_{C1}$-$R_{C4}$ and $R_{T1}$-$R_{T4}$ of split bridge halves in simplified block diagram form, and shows mechanically isolated measurement output lead lines L1'-L4' extending between the strain gauge elements of the split bridge halves and shows input signal lead line L5' electrically coupling $R_{C1}$, $R_{C2}$, $R_{T1}$ and $R_{T2}$ at a node $V_I^+$ and shows input signal lead line L6' electrically coupling $R_{C3}$, $R_{C4}$, $R_{T3}$ and $R_{T4}$ at a node $V_I^-$. FIG. 20B illustrates details of a first example arrangement of the strain gauge elements $R_{C1}$-$R_{C4}$ and $R_{T1}$-$R_{T4}$ of the example sensor of FIG. 20A. FIG. 20C illustrates details of a second example arrangement of the strain gauge elements $R_{C1}$-$R_{C4}$ and $R_{T1}$-$R_{T4}$ of the example sensor 2000 of FIG. 20A. To simplify the drawings, the mechanically isolated measurement output lead lines L1'-L4' and input lead lines L5-L6 are omitted from FIGS. 20B-20C, although their interconnections are explained below.

Referring to FIG. 20A, mechanically isolated measurement output lead lines L1'-L4' of FIG. 20A correspond to correspondingly labeled integral measurement output lead lines L1-L4 of FIG. 19. The mechanically isolated lead lines L1'-L4' are routed externally off the beam, one example of this implementation is to have the leads L1'-L6' be part of a flex circuit/cable that is wirebonded to the beam. The flex cable will be mounted such that it has enough slack that the deflection of the beam due to force applied doesn't produce any strain the flex circuit/cable, moreover the lead lines on the flex circuit can be made of lower resistance electrical material, such as Copper in comparison to the higher resistance thin film material, such as Nichrome (an alloy of Nickel and Chromium), thus providing a lowerer magnitude the lead resistances. Thus, the lead lines L1'-L4' that electrically couple the strain gauge elements are mechanically isolated from strain imparted during deflection of the beam 2002 due to a deflecting force (not shown) applied to the beam.

Referring to the example two-bridge arrangement FIG. 20B, except for the change in lead lines, the arrangement of the example force sensor 2000 of FIG. 20B is identical to that of the sensor of FIG. 19. Elongated measurement output lead lines L1'-L4' and input lead lines L5-L6 are mechanically isolated from the beam and shorter integral proximal lead line segments $X_{P1}$-$X_{P6}$ and shorter integral distal lead line segments $X_{D1}$-$X_{D6}$ are disposed integral with the beam. As a result, less stress is imparted to the leads during mechanical deflection of the beam, and therefore, less strain measurement distortion is incurred when compared with the example sensor of FIG. 19.

Mechanically isolated lead line L1' is disposed to extend in mechanical isolation from the beam between the proximal, center and distal portions of the beam, to electrically couple $R_{C1}$ and $R_{C2}$ at nodes labeled $V_{O1}$− in the proximal and distal bridge halves. Isolated lead line L2' is disposed to extend in mechanical isolation from the beam between the proximal, center and distal portions of the beam, to electrically couple $R_{T1}$ and $R_{T3}$ at nodes labeled $V_{O1}$+ in the proximal and distal bridge halves. Isolated lead line L3' is disposed to extend in mechanical isolation from the beam between the proximal, center and distal portions of the beam, to electrically couple $R_{C2}$ and Rea at nodes labeled $V_{O2}$− in the proximal and distal bridge halves. Isolated lead line L4' is disposed to extend in mechanical isolation from the beam between the proximal, center and distal portions of the beam, to electrically couple $R_{T2}$ and $R_{T4}$ at nodes labeled $V_{O2}^+$ in the proximal and distal bridge halves. Proximal lead line elements $X_{P3}$-$X_{P4}$ are coupled to voltage $V_I^+$ to thereby electrically couple $R_{C1}$, $R_{C2}$, $R_{T1}$ and $R_{T2}$ at the voltage $V_I^+$. Distal lead line elements $X_{D3}$-$X_{D4}$ are coupled to voltage $V_I$+ to thereby electrically couple $R_{C3}$, $R_{C4}$, $R_{T3}$ and $R_{T4}$ to the voltage $V_I^+$.

Referring to the example two-bridge arrangement FIG. 20C, each of the compression gauge resistors and each of the tension gauge resistors is arranged symmetrically about the neutral axis 2004 of the beam. Moreover, in the second example arrangement, $R_{C1}$ and $R_{T1}$ of the proximal half of the first bridge and $R_{C2}$ and $R_{T2}$ of the proximal half of the second bridge are arranged symmetrically about a proximal transverse axis 2006P between them at the proximal portion of the beam. $R_{C2}$ partially surrounds $R_{C1}$, and $R_{T2}$ partially surrounds $R_{C2}$. Terminals of $R_{C1}$ and $R_{T2}$ are transversely aligned proximate to the proximal transverse axis 2006P, and terminals of $R_{C2}$ and $R_{T2}$ are transversely aligned distal to the proximal transverse axis 2006P. Likewise, $R_{C3}$ and $R_{T3}$ of the distal half of the first bridge and $R_{C4}$ and $R_{T4}$ of the distal half of the second bridge are further arranged symmetrically about a distal transverse axis 2006D between them at the distal portion of the beam. Terminals of $R_{C3}$ and $R_{T3}$ are transversely aligned proximate to the distal transverse axis 2006D, and terminals of $R_{C4}$ and $R_{T4}$ are transversely aligned distal to the distal transverse axis 2006D. $R_{C3}$ partially surrounds $R_{C3}$, and $R_{T4}$ partially surrounds $R_{C4}$.

Still referring to FIG. 20C, elongated lead line segments L1'-L4' are mechanically isolated from the beam and shorter integral proximal lead line segments $X_{P7}$-$X_{P8}$ and shorter integral distal lead line segments $X_{D7}$-$X_{D8}$ are disposed integral with the beam. As a result, less stress is imparted to the leads during mechanical deflection of the beam, and therefore, less strain measurement distortion is incurred when compared with the example sensor of FIG. 19.

The coupling between nodes and lead lines is the same for the first and second example arrangements of FIGS. 20B-20C. More specifically, referring to FIG. 20C, mechanically isolated lead line L1' is disposed to extend in mechanical isolation from the beam between the proximal, center and distal portions of the beam, to electrically couple $R_{C1}$ and $R_{C3}$ at nodes labeled $V_{O1}$− in the proximal and distal bridge halves. Isolated lead line L2' is disposed to extend in mechanical isolation from the beam between the proximal, center and distal portions of the beam, to electrically couple $R_{T1}$ and $R_{T3}$ at nodes labeled $V_{O1}$+ in the proximal and distal bridge halves. Isolated lead line L3' is disposed to extend in mechanical isolation from the beam between the proximal, center and distal portions of the beam, to electrically couple $R_{C2}$ and $R_{C4}$ at nodes labeled $V_{O2}$− in the proximal and distal bridge halves. Isolated lead line L4' is disposed to extend in mechanical isolation from the beam between the proximal, center and distal portions of the beam, to electrically couple $R_{T2}$ and $R_{T4}$ at nodes labeled $V_{O2}^+$ in the proximal and distal bridge halves. Proximal lead line elements $X_{P7}$-$X_{P8}$ are coupled to voltage $V_I$+ to thereby electrically couple $R_{C1}$, $R_{C2}$, $R_{T1}$ and $R_{T2}$ at the voltage $V_I$+. Distal lead line elements $X_{D7}$-$X_{D8}$ are coupled to voltage $V_I^+$ to thereby electrically couple $R_{C3}$, $R_{C4}$, $R_{T3}$ and $R_{T4}$ to the voltage $V_I^+$.

Figure 21:
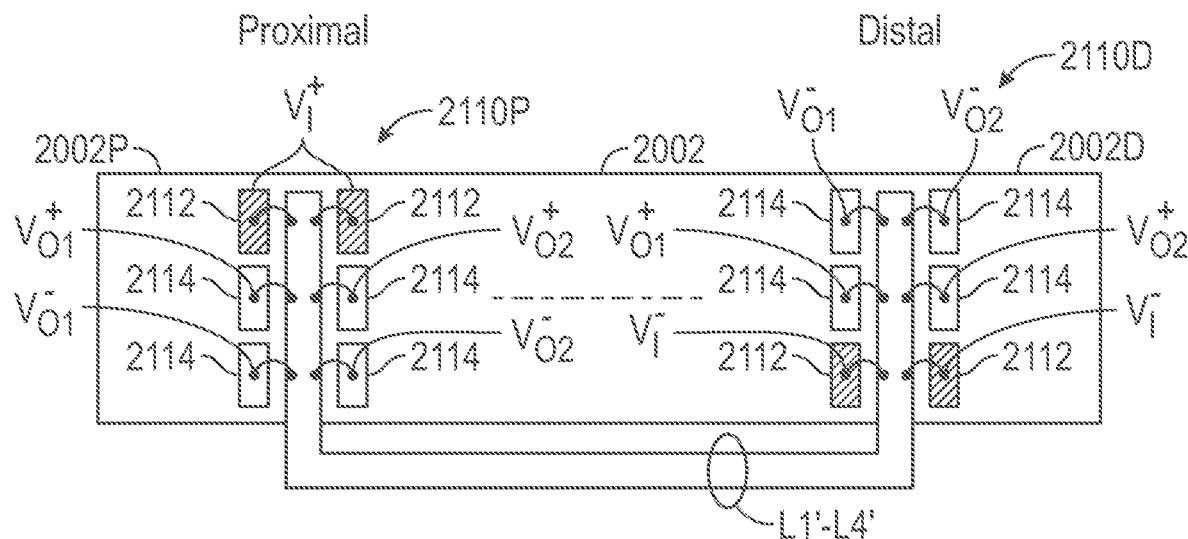
FIG. 21 is an illustrative drawing showing a set of proximal connection pads and a set of distal connection pads in which input pads and measurement pads have matching areas.

FIG. 21 is an illustrative drawing showing a set of proximal connection pads 2110P and a set of distal connection pads 2110D disposed upon the beam 2002 of FIG. 20A in which input pads 2112 and measurement pads 2114 have matching areas. The set of proximal connection pads 2110P and the set of distal connection pads 2110D are disposed upon an example beam 2002 for electrical coupling of mechanically isolated measurement output lead lines L1'-L4' and input signal lines L5'-L6' to the strain gauge resistors. Wire bonds (they are there in FIG. 21 it is the small arc going from the pads to the collection of lead lines. Also please include L5-L6 to bundle of leads) electrically couple the measurement output leads L1'-L4' to the pads measurement pads 2114 and to couple the input signal leads L5'-L6' to the input pads 2112. Input signal pads 2112 are coupled to receive the excitation voltage $V_I^+$, $V_I^-$, as shown. Measurement output pads 2114 are coupled to receive the sensed output voltages $V_{O1}^-$, $V_{O1}^+$, $V_{O2}^-$, $V_{O2}^+$, as shown.

Conventionally, all pads typically are the same area, and therefore, have the same resistance. The wire bonds can be variable, however, which can impact the resistance of the electrical connection between the pads and the leads, which in turn, can influence zero offset between signals on the different electrical leads and also may influence temperature sensitivity of the electrical connection. Increased resistance at the input pads affects gain of the voltage, which is related to sensitivity of measurement. Increased resistance at the output measurement pads affects the zero offset. In general, gain can be more easily managed than zero offset, using software, for example.

Figure 22:
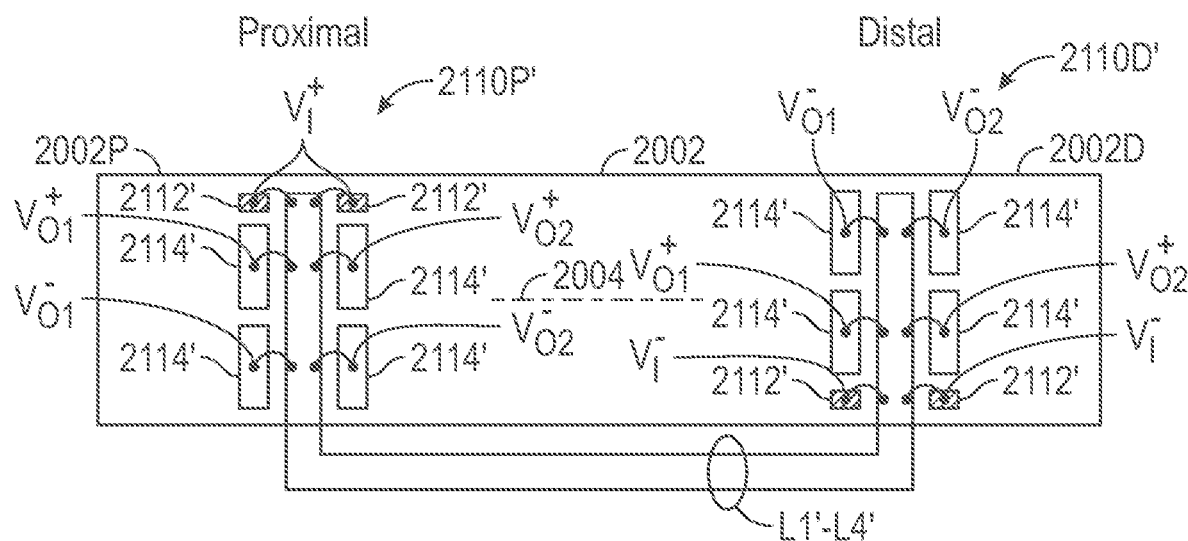
FIG. 22 is an illustrative drawing showing a set of proximal connection pads and a set of distal connection pads in which measurement pads have larger area than input pads.

FIG. 22 is an illustrative drawing showing a set of proximal connection pads 2110P' and a set of distal connection pads 2110D' in which measurement output pads 2114' have larger area than input signal pads 2112'. Input pad area is sacrificed to provide larger measurement pad area. The larger measurement pad area results in reduced resistance of the measurement pads 2114', which reduces the impact of wire bond variation upon connection pad resistance, which in turn, reduces the impact of wire bond variation upon zero offset. Thus, a relative increase in measurement pad size compared with input signal pad size reduces variability of measurement pad resistance reducing the impact of variation in location and size of a wire bond upon measurement accuracy.

Still referring to FIG. 22, the set of proximal connection pads 2110P' and the set of distal connection pads 2110D' are disposed upon an example beam 2002 for electrical coupling of mechanically isolated lead lines L1'-L4' and L5'-L6' to strain gauge resistors. Wire bonds electrically couple the leads L1'-L4' to the measurement output pads 2114'. Input signal pads 2112' are coupled to receive the excitation voltage $V_I^+$, $V_I^-$, as shown. Measurement signal output pads 2114' are coupled to receive the sensed output voltages $V_{O1}^-$, $V_{O1}^+$, $V_{O2}^-$, $V_{O2}^+$, as shown.

Figure 23:
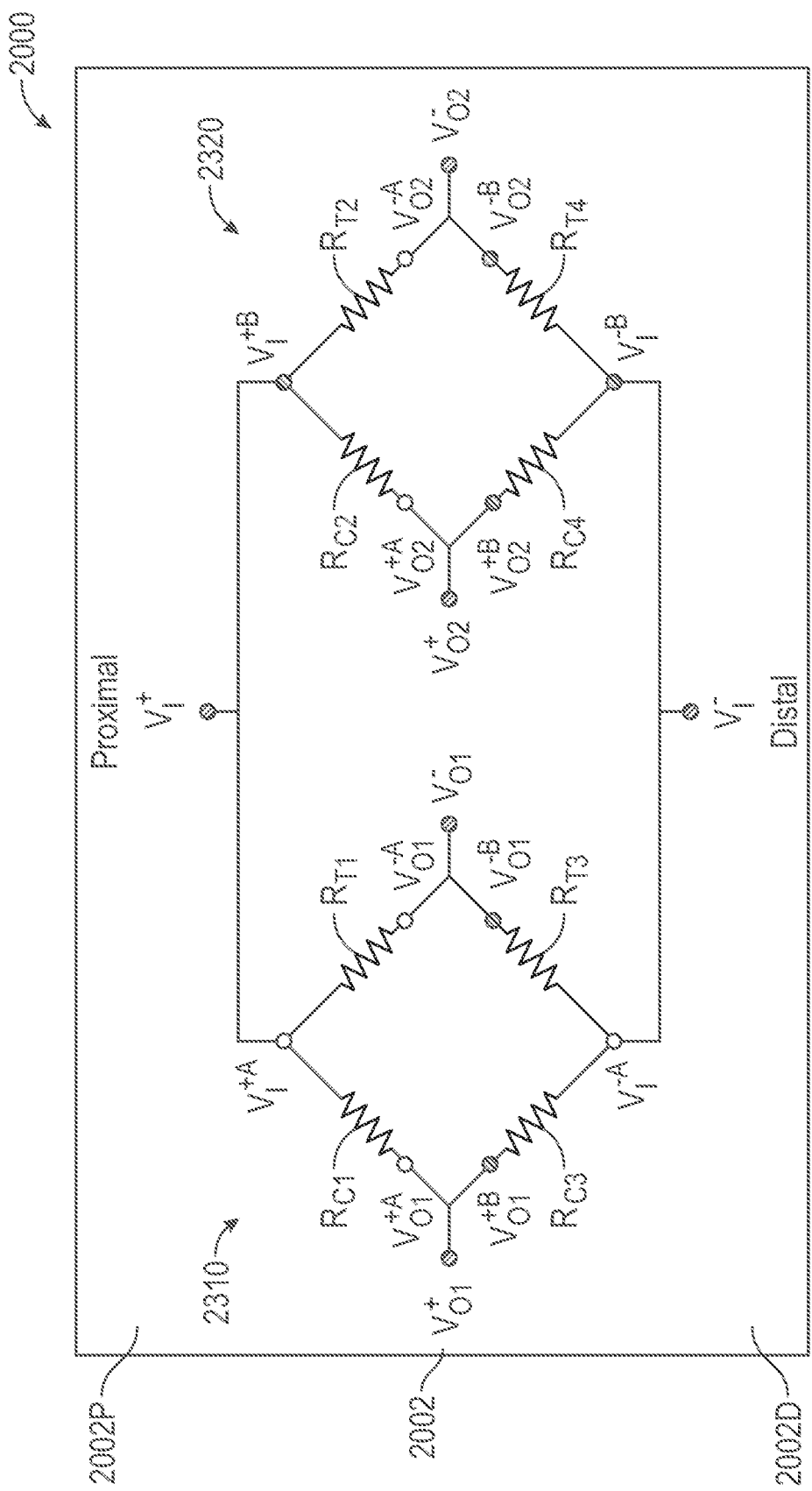
FIG. 23 is an illustrative circuit schematic showing a force sensor that includes example first and second split bridge circuits disposed upon a beam that share excitation voltage inputs.

FIG. 23 is an illustrative circuit schematic showing a force sensor 2000 that includes example first and second split bridge circuits 2310, 2320 disposed upon a beam that share excitation voltage inputs $V_I^+$, $V_I^-$. Half of each bridge circuit is disposed at a proximal end portion of the beam, and half of each bridge circuit is disposed at a distal portion of the beam. To simplify the drawing, however, FIG. 23 does not show the physical separation of the proximal and distal halves at opposite end portions of the beam. FIG. 23 shows the example arrangement of the first and second split bridge circuits at non-overlapping separate locations upon the beam. FIG. 5 shows an example staggered arrangement of the first and second split bridge circuits. FIG. 6 shows an example interleaved arrangement of the first and second split bridge circuits.

As explained above, measurement redundancy is achieved using two split bridge circuits, each having a half-bridge disposed at the proximal end portion of the beam and having a half-bridge portion disposed at the distal end portion of the beam. For example, a mismatch of corresponding output measurements of the two split bridge circuits is indicative of measurement error and possible damage of one or both of the two bridge circuits. To ensure accuracy in determination of measurement mismatches, for example, the resistance of corresponding tap lead lines for first and second bridge circuits should match.

Figure 24:
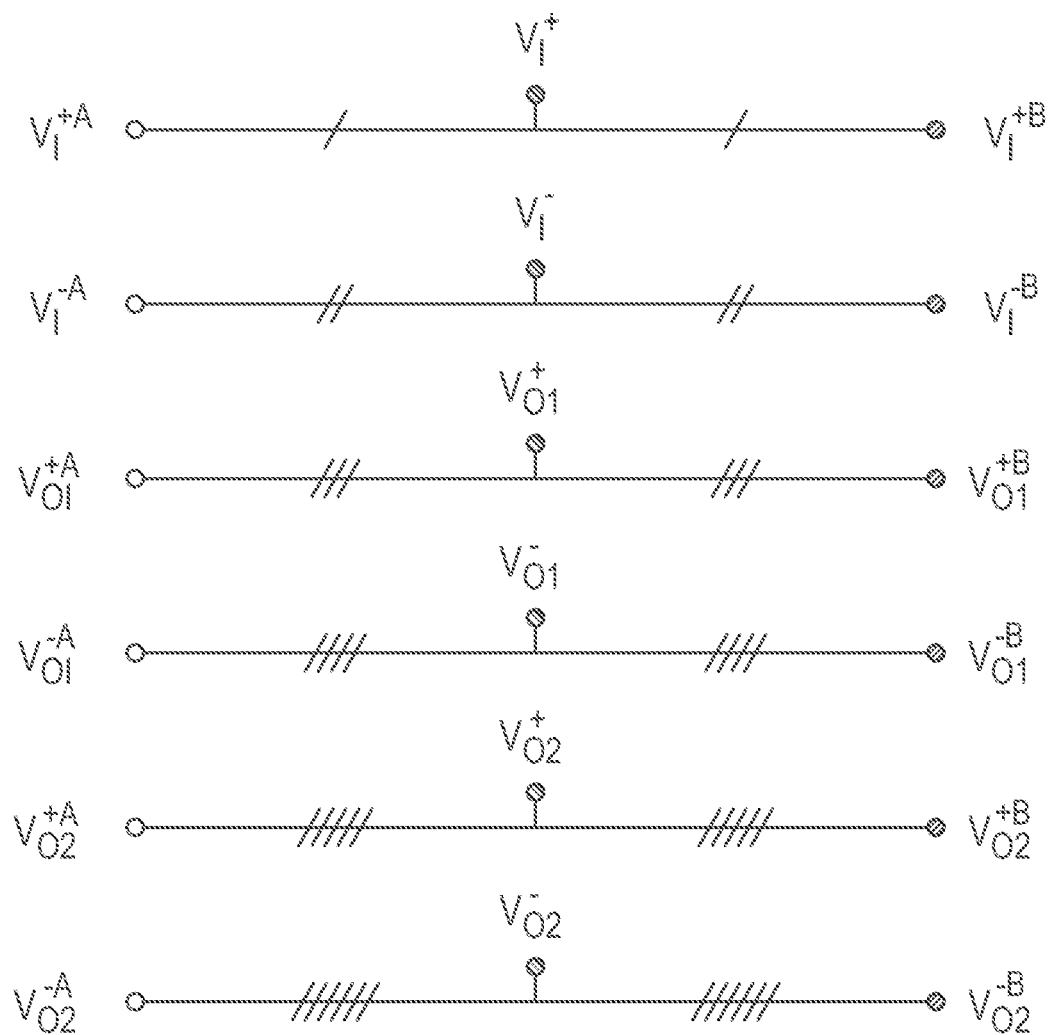
FIG. 24 is an illustrative drawing representing the tap lead lines for the example dual split bridge circuit of FIG. 23.

FIG. 24 is an illustrative drawing representing the tap lead lines for the example dual split bridge circuit of FIG. 23. Tap lead lines between a voltage level and a circuit node have equal lead line lengths and have uniform line widths to provide matching resistance between a given tap point and each of the circuit nodes electrically coupled to the tap point. Thus, resistances between each tap point and the nodes electrically coupled to the tap point is balanced.

In particular, for example, the tap lead line length and lead line width between tap point of excitation input voltage $V_I^+$ and the circuit node receiving $V_I^{+A}$ equals the tap lead line length and lead line width between tap point of voltage $V_I^+$ and circuit node receiving $V_I^{+B}$ as indicated by the single hash marks on either side of the $V_I^+$ tap point.

The tap lead line length and lead line width between tap point of excitation input voltage $V_I^-$ and the circuit node receiving $V_I^{-A}$ equals the tap lead line length and lead line width between tap point of voltage $V_I^-$ and circuit node receiving $V_I^{-B}$ as indicated by the double hash marks on either side of the $V_I^-$ tap point.

The tap lead line length and lead line width between tap point of measurement voltage $V_{O1}^+$ and the circuit node providing $V_{O1}^{-A}$ equals the tap lead line length and lead line width between tap point of voltage $V_{O1}^+$ and circuit node receiving $V_{O1}^{+B}$ as indicated by the three hash marks on either side of the $V_{O1}^+$ tap point.

The tap lead line length and lead line width between tap point of measurement voltage $V_{O1}^-$ and the circuit node providing $V_{O1}^{-A}$ equals the tap lead line length and lead line width between tap point of voltage $V_{O1}^-$ and circuit node receiving $V_{O1}^{-B}$ as indicated by the four hash marks on either side of the $V_{O1}^-$ tap point.

The tap lead line length and lead line width between tap point of measurement voltage VO2+ and the circuit node providing VO2+A equals the tap lead line length and lead line width between tap point of voltage VO2+ and circuit node receiving VO2+B as indicated by the five hash marks on either side of the VO2+ tap point.

The tap lead line length and lead line width between tap point of measurement voltage VO2− and the circuit node providing VO2−A equals the tap lead line length and lead line width between tap point of voltage VO2− and circuit node receiving VO2−B as indicated by the five hash marks on either side of the VO2− tap point.

The equal tap lead line length ensures balanced tap line lead length resistance on each side of each tap point resulting in more accurate determinations of circuit damage based upon measurement output signal mismatches, for example.

Although illustrative examples have been shown and described, a wide range of modification, change and substitution is contemplated in the foregoing disclosure and in some instances, some features of the examples may be employed without a corresponding use of other features. One of ordinary skill in the art would recognize many variations, alternatives, and modifications. Thus, the scope of the disclosure should be limited only by the following claims, and it is appropriate that the claims be construed broadly and in a manner consistent with the scope of the examples disclosed herein. The above description is presented to enable any person skilled in the art to create and use a force sensor with a beam and a distributed bridge circuit. Various modifications to the examples will be readily apparent to those skilled in the art, and the generic principles defined herein may be applied to other examples and applications without departing from the scope of the invention. In the preceding description, numerous details are set forth for the purpose of explanation. However, one of ordinary skill in the art will realize that the invention might be practiced without the use of these specific details. In other instances, well-known processes are shown in block diagram form in order not to obscure the description of the invention with unnecessary detail. Identical reference numerals may be used to represent different views of the same or similar item in different drawings. Thus, the foregoing description and drawings of examples in accordance with the present invention are merely illustrative of the principles of the invention. Therefore, it will be understood that various modifications can be made to the examples by those skilled in the art without departing from the scope of the invention, which is defined in the appended claims.

What is claimed is:

1. A force sensor comprising:
a beam including a proximal end portion, a distal end portion, and a first face between the proximal end portion of the beam and the distal end portion of the beam;
a first bridge circuit on the first face of the beam, the first bridge circuit including a first tension strain gauge resistor, a second tension strain gauge resistor, a first compression strain gauge resistor, and a second compression strain gauge resistor, the first tension strain gauge resistor and the first compression strain gauge resistor being located at the proximal end portion of the beam, the second tension strain gauge resistor and the second compression strain gauge resistor being located at the distal end portion of the beam;
a first measurement signal lead line electrically coupled to a first measurement signal pad, the first measurement signal lead line electrically coupling the first compression strain gauge resistor and the second compression strain gauge resistor;
a second measurement signal lead line electrically coupled to a second measurement signal pad, the second measurement signal lead line electrically coupling the first tension strain gauge resistor and the second tension strain gauge resistor;

a first input signal tap line electrically coupled to a first input signal pad, the first compression strain gauge resistor and the first tension strain gauge resistor being electrically coupled to receive a first input signal via the first input signal tap line, an area of the first input signal pad being less than an area of the first measurement signal pad; and a second input signal tap line electrically coupled to a second input signal pad, the second compression strain gauge resistor and the second tension strain gauge resistor are electrically coupled to receive a second input signal via the second input signal tap line, an area of the second input signal pad being less than an area of the second measurement signal pad.

2. The force sensor of claim 1, wherein:
the first input signal pad is wire bonded to the first input signal tap line;
the second input signal pad is wire bonded to the second input signal tap line;
the first measurement signal pad is wire bonded to the first measurement signal lead line; and
the second measurement signal pad is wire bonded to the first measurement signal lead line.

3. The force sensor of claim 1, wherein:
the force sensor further includes a second bridge circuit on the first face of the beam, a third measurement signal lead line, and a fourth measurement signal lead line;
the second bridge circuit includes a third tension strain gauge resistor, a fourth tension strain gauge resistor, a third compression strain gauge resistor, and a fourth compression strain gauge resistor;
the third tension strain gauge resistor and the third compression strain gauge resistor are located at the proximal end portion of the beam;
the fourth tension strain gauge resistor and the fourth compression strain gauge resistor are located at the distal end portion of the beam;
the third measurement signal lead line electrically couples the third compression strain gauge resistor and the fourth compression strain gauge resistor; and
the fourth measurement signal lead line electrically couples the third tension strain gauge resistor and the fourth tension strain gauge resistor.

4. The force sensor of claim 3, wherein:
a longitudinal axis extends between the proximal end portion of the beam and the distal end portion of the beam;
a neutral axis extends in the first face of the beam parallel to the longitudinal axis and equidistant from opposite edges of the first face;
each of the first, second, third, and fourth compression strain gauge resistors is symmetrically located about the neutral axis; and
each of the first, second, third, and fourth tension strain gauge resistors is symmetrically located about the neutral axis.

5. The force sensor of claim 3, wherein:
a longitudinal axis extends between the proximal end portion of the beam and the distal end portion of the beam;
a neutral axis extends in the first face of the beam parallel to the longitudinal axis and equidistant from opposite edges of the first face;
each of the first, second, third, and fourth compression strain gauge resistors is identically symmetrically located about the neutral axis; and
each of the first, second, third, and fourth tension strain gauge resistors is identically symmetrically located about the neutral axis.

6. The force sensor of claim 3, wherein:
the force sensor further includes a third measurement signal pad and a fourth measurement signal pad;
the first compression strain gauge resistor, the first tension strain gauge resistor, the third compression strain gauge resistor, and the third tension strain gauge resistor are electrically coupled to the first input signal pad via the first input signal tap line;
the second compression strain gauge resistor, the second tension strain gauge resistor, the fourth compression strain gauge resistor, and the fourth tension strain gauge resistor are electrically coupled to the second input signal pad via the second input signal tap line;
the third measurement signal pad is electrically coupled to the third measurement signal lead line;
the fourth measurement signal pad is electrically coupled to the third measurement signal lead line; and
an individual area of the first input signal pad and an individual area of the second input signal pad are each less than each of an individual area of the first measurement signal pad, an individual area of the second measurement signal pad, an individual area of the third measurement signal pad, and an individual area of the fourth measurement signal pad.

7. The force sensor of claim 3, wherein:
a proximal transverse axis extends between the first compression strain gauge resistor and the third compression strain gauge resistor;
a distal transverse axis extending between the second compression strain gauge resistor and the fourth compression strain gauge resistor;
the first tension strain gauge resistor and the first compression strain gauge resistor are located proximally relative to the proximal transverse axis;
the second tension strain gauge resistor and the second compression strain gauge resistor are located proximally relative to the distal transverse axis;
the third compression strain gauge resistor and the third tension strain gauge resistor are located distally relative to the proximal transverse axis; and
the fourth compression strain gauge resistor and the fourth tension strain gauge resistor are located distally relative to the proximal transverse axis.

8. A force sensor comprising:
a beam including a proximal end portion, a distal end portion, and a first face between the proximal end portion of the beam and the distal end portion of the beam;
a first bridge circuit on the first face of the beam, the first bridge circuit including a first tension strain gauge resistor, a second tension strain gauge resistor, a first compression strain gauge resistor, and a second compression strain gauge resistor;
a second bridge circuit on the first face of the beam, the second bridge circuit including a third tension strain gauge resistor, a fourth tension strain gauge resistor, a third compression strain gauge resistor, and a fourth compression strain gauge resistor;
a first measurement signal lead line electrically coupled to a first measurement signal pad, the first measurement signal lead line electrically coupling the first compression strain gauge resistor and the second compression strain gauge resistor;
a second measurement signal lead line electrically coupled to a second measurement signal pad, the second measurement signal lead line electrically coupling the first tension strain gauge resistor and the second tension strain gauge resistor;
a third measurement signal lead line electrically coupled to a third measurement signal pad, the third measurement signal lead line electrically coupling the third compression strain gauge resistor and the fourth compression strain gauge resistor;
a fourth measurement signal lead line electrically coupled to a fourth measurement signal pad, the fourth measurement signal lead line electrically coupling the third tension strain gauge resistor and the fourth tension strain gauge resistor;
a first input signal tap line electrically coupled to a first input signal pad, the first compression strain gauge resistor, the first tension strain gauge resistor, the third compression strain gauge resistor, and the third tension strain gauge resistor being electrically coupled to receive a first input signal via the first input signal tap line; and
a second input signal tap line electrically coupled to a second input signal pad, the second compression strain gauge resistor, the second tension strain gauge resistor, the fourth compression strain gauge resistor and the fourth tension strain gauge resistor are electrically coupled to receive a second input signal via the second input signal tap line, an individual area of the first input signal pad and an individual area of the second input signal pad being each less than each of an individual area of the first measurement signal pad, an individual area of the second measurement signal pad, an individual area of the third measurement signal pad, and an individual area of the fourth measurement signal pad.

9. The force sensor of claim 8, wherein:
a resistance of the first measurement signal lead line between the first measurement signal pad point and the first compression strain gauge resistor matches a resistance of the first measurement signal lead line between the first measurement signal pad and the second compression strain gauge resistor;
a resistance of the second measurement signal lead line between the second measurement signal pad and the first tension strain gauge resistor matches a resistance of the second measurement signal lead line between the second measurement signal pad and the second tension strain gauge resistor;
a resistance of the third measurement signal lead line between the third measurement signal pad and the third compression strain gauge resistor matches a resistance of the third measurement signal lead line between the third measurement signal pad and the fourth compression strain gauge resistor; and
a resistance of the fourth measurement signal lead line between the fourth measurement signal pad and the third tension strain gauge resistor matches a resistance of the fourth measurement signal lead line between the fourth measurement signal pad and the fourth tension strain gauge resistor.

10. The force sensor of claim 8, wherein:
resistances of the first input signal tap line are matched between the first input signal pad and a junction of the first compression strain gauge resistor and the first tension strain gauge resistor and between the first input signal pad and a junction of the third compression strain gauge resistor and the third tension strain gauge resistor; and
resistances of the second input signal tap line are matched between the second input signal pad and a junction of the first compression strain gauge resistor and the first tension strain gauge resistor and between the second input signal pad and a junction of the third compression strain gauge resistor and the third tension strain gauge resistor.

11. The force sensor of claim 10, wherein:
the first input signal pad is wire bonded to the first input signal tap line;
the second input signal pad is wire bonded to the second input signal tap line;
the first measurement signal pad is wire bonded to the first measurement signal lead line;
the second measurement signal pad is wire bonded to the first measurement signal lead line;
the third measurement signal pad is wire bonded to the third measurement signal lead line; and
the fourth measurement signal pad is wire bonded to the third measurement signal lead line.

12. The force sensor of claim 8, wherein:
a longitudinal axis extends between the proximal end portion of the beam and the distal end portion of the beam;
a neutral axis extends in the first face of the beam parallel to the longitudinal axis and equidistant from opposite edges of the first face;
each of the first, second, third, and fourth compression strain gauge resistors is symmetrically located about the neutral axis; and
each of the first, second, third and fourth tension strain gauge resistors is symmetrically located about the neutral axis.

13. The force sensor of claim 8, wherein:
a longitudinal axis extends between the proximal end portion of the beam and the distal end portion of the beam;
a neutral axis that extends in the first face of the beam parallel to the longitudinal axis and equidistant from opposite edges of the first face;
each of the first, second, third, and fourth compression strain gauge resistors is identically symmetrically located about the neutral axis; and
each of the first, second, third, and fourth tension strain gauge resistors is identically symmetrically located about the neutral axis.

14. The force sensor of claim 8, wherein:
a proximal transverse axis extends between the first compression strain gauge resistor and the third compression strain gauge resistor;
a distal transverse axis extends between the second compression strain gauge resistor and the fourth compression strain gauge resistor;
the first tension strain gauge resistor and the first compression strain gauge resistor are located proximally relative to the proximal transverse axis;
the third compression strain gauge resistor and the third tension strain gauge resistor are located distally relative to the proximal transverse axis;
the second tension strain gauge resistor and the second compression strain gauge resistor are located proximally relative to the distal transverse axis; and the fourth compression strain gauge resistor and the fourth tension strain gauge resistor are located distally relative to the proximal transverse axis.

15. A force sensor comprising:
a beam including a proximal end portion, a distal end portion, and a first face between the proximal end portion of the beam and the distal end portion of the beam;
a first bridge circuit on the first face of the beam, the first bridge circuit including a first plurality of strain gauge resistors;
a second bridge circuit on the first face of the beam, the second bridge circuit including a second plurality of strain gauge resistors;
a first measurement signal lead line electrically coupled to the first bridge circuit via a first measurement signal pad;
a second measurement signal lead line electrically coupled to the first bridge circuit via a second measurement signal pad;
a third measurement signal lead line electrically coupled to the second bridge circuit via a third measurement signal pad;
a fourth measurement signal lead line electrically coupled to the second bridge circuit via a fourth measurement signal pad;
a first input signal tap line electrically coupled to the first bridge circuit and the second bridge circuit via a first input signal pad; and
a second input signal tap line electrically coupled to the first bridge circuit and the second bridge circuit via a second input signal pad, an individual area of the first input signal pad and an individual area of the second input signal pad being each less than each of an individual area of the first measurement signal pad, an individual area of the second measurement signal pad, an individual area of the third measurement signal pad, and an individual area of the fourth measurement signal pad.

16. The force sensor of claim 15, wherein:
the first plurality of strain gauge resistors includes a plurality of tension strain gauge resistors; and
the second plurality of strain gauge resistors includes a plurality of tension strain gauge resistors.

17. The force sensor of claim 15, wherein:
the first input signal pad is wire bonded to the first input signal tap line;
the second input signal pad is wire bonded to the second input signal tap line;
the first measurement signal pad is wire bonded to the first measurement signal lead line;
the second measurement signal pad is wire bonded to the first measurement signal lead line;
the third measurement signal pad is wire bonded to the third measurement signal lead line; and
the fourth measurement signal pad is wire bonded to the third measurement signal lead line.

18. The force sensor of claim 15, wherein:
a longitudinal axis extends between the proximal end portion of the beam and the distal end portion of the beam;
a neutral axis extends in the first face of the beam parallel to the longitudinal axis and equidistant from opposite edges of the first face;
the first plurality of strain gauge resistors is positioned symmetrically about the neutral axis; and
the second plurality of strain gauge resistors is positioned symmetrically about the neutral axis.

19. The force sensor of claim 15, wherein:
the first plurality of strain gauge resistors includes a first tension strain gauge resistor positioned at the proximal end portion of the beam and a second tension strain gauge resistor positioned at the distal end portion of the beam; and
the second plurality of strain gauge resistors includes a third tension strain gauge resistor positioned at the proximal end portion of the beam and a fourth tension strain gauge resistor positioned at the distal end portion of the beam.

20. The force sensor of claim 19, wherein:
the first tension strain gauge resistor is positioned at a longitudinal position between the third tension strain gauge resistor and the fourth tension strain gauge resistor; and
the fourth tension strain gauge resistor is positioned at a longitudinal position between the first tension strain gauge resistor and the second tension strain gauge resistor.

* * * * *